US009839627B2

(12) United States Patent
McKinney et al.

(10) Patent No.: US 9,839,627 B2
(45) Date of Patent: Dec. 12, 2017

(54) METHODS OF TREATING FRAGILE X ASSOCIATED DISORDERS, ADHD, AND AUTISM SPECTRUM DISORDER

(71) Applicant: Neurovance, Inc., Princeton, NJ (US)

(72) Inventors: Anthony McKinney, Cambridge, MA (US); Frank Gentile, Boxborough, MA (US); Timothy Hsu, Cambridge, MA (US); Franklin Bymaster, Brownsburg, IN (US); Walter Piskorski, Nashua, NH (US); Richard Welter, Las Cruces, NM (US)

(73) Assignee: NEUROVANCE, INC., Princeton, NJ (US)

( * ) Notice: Subject to any disclaimer, the term of this patent is extended or adjusted under 35 U.S.C. 154(b) by 0 days.

(21) Appl. No.: 15/102,871

(22) PCT Filed: Dec. 9, 2014

(86) PCT No.: PCT/US2014/069401
§ 371 (c)(1),
(2) Date: Jun. 9, 2016

(87) PCT Pub. No.: WO2015/089111
PCT Pub. Date: Jun. 18, 2015

(65) Prior Publication Data
US 2016/0303076 A1    Oct. 20, 2016

Related U.S. Application Data

(60) Provisional application No. 61/913,886, filed on Dec. 9, 2013.

(51) Int. Cl.
| | | |
|---|---|---|
| *A61K 31/403* | (2006.01) | |
| *A61K 45/06* | (2006.01) | |
| *A61K 31/185* | (2006.01) | |
| *A61K 31/27* | (2006.01) | |
| *A61K 31/65* | (2006.01) | |
| *A61K 9/20* | (2006.01) | |

(52) U.S. Cl.
CPC .......... *A61K 31/403* (2013.01); *A61K 9/2013* (2013.01); *A61K 9/2018* (2013.01); *A61K 9/2054* (2013.01); *A61K 31/185* (2013.01); *A61K 31/27* (2013.01); *A61K 31/65* (2013.01); *A61K 45/06* (2013.01)

(58) Field of Classification Search
CPC .. A61K 31/403; A61K 9/2018; A61K 9/2013; A61K 9/2054; A61K 31/65; A61K 31/27; A61K 31/185; A61K 45/06
See application file for complete search history.

(56) References Cited

U.S. PATENT DOCUMENTS

| | | | |
|---|---|---|---|
| 8,461,196 | B2 | 6/2013 | Skolnick et al. |
| 8,877,798 | B2 | 11/2014 | Skolnick et al. |
| 9,205,074 | B2 | 12/2015 | Skolnick et al. |
| 2007/0082940 | A1 | 4/2007 | Skolnick et al. |
| 2008/0058535 | A1 | 3/2008 | Chen et al. |
| 2011/0034565 | A1 | 2/2011 | Regan et al. |
| 2012/0258994 | A1 | 10/2012 | McKinney et al. |
| 2014/0206740 | A1 | 7/2014 | McKinney et al. |
| 2014/0228421 | A1 | 8/2014 | McKinney et al. |
| 2016/0158197 | A1 | 6/2016 | Skolnick et al. |
| 2016/0199347 | A1 | 7/2016 | McKinney et al. |
| 2016/0303077 | A1 | 10/2016 | McKinney et al. |
| 2016/0368871 | A1 | 12/2016 | McKinney et al. |

FOREIGN PATENT DOCUMENTS

| | | | |
|---|---|---|---|
| WO | WO 2006/096810 A2 | 9/2006 | |
| WO | WO 2007/014264 A2 | 2/2007 | |
| WO | WO 2007/016155 A2 | 2/2007 | |
| WO | WO 2008/013856 A2 | 1/2008 | |
| WO | WO 2012/118563 A2 | 9/2012 | |
| WO | WO 2013019271 A1 * | 2/2013 | ........... A61K 31/403 |
| WO | WO 2015/102826 A1 | 7/2015 | |
| WO | WO 2016/205762 A1 | 12/2016 | |

OTHER PUBLICATIONS

Gallagher et al (J.Neurol., 2012, 259:401-413).*
U.S. Appl. No. 13/605,890, filed Sep. 6, 2012, McKinney.
U.S. Appl. No. 13/334,066, filed Dec. 22, 2011, McKinney et al.
Bailey, D. et al., "Medication Utilization for Targeted Symptoms in Children and Adults With Fragile X Syndrome: US Survey," Journal of Developmental & Behavioral Pediatrics, 2012, 33 (1), 62-69.
Berry-Kravis, E. et al., "Clinic-Based Retrospective Analysis of Psychopharmacology for Behavior in Fragile X Syndrome," International Journal of Pediatrics, 2012, Article ID 843016, 11 pages, doi:10.1155/2012/843016.
Bymaster, F. et al., "Pharmacological Characterization of the Norepinephrine and Dopamine Reuptake Inhibitor EB-1020: Implications for Treatment of Attention-Deficit Hyperactivity Disorder," Synapse, 2012, 66, 522-532.
Consensus of the Fragile X Clinical & Research Consortium on Clinical Practices, "Medications for Individuals with Fragile X Syndrome," dated 2012, 10 pages, [retrieved on May 8, 2017]. Retrieved from the Internet <URL: https://fragilex.org/wp-content/uploads/2012/08/Medications_for_Individuals_with_Fragile_X_Syndrome2012-Oct.pdf>.
Hartley, S. et al., "Exploring the Adult Life of Men and Women with Fragile X Syndrome: Results from a National Survey," NIH Public Access, Author Manuscript, available in PMC Dec. 15, 2011, face of article states: Published in final edited form as: *Am J Intellect Dev Disabil*. Jan. 2011; 116(1): 16-35, doi:10.1352/1944-7558-116.1.16, 24 pages.
International Preliminary Report on Patentability for International Application No. PCT/US2014/069401, dated Jun. 14, 2016, 16 pages.

(Continued)

*Primary Examiner* — Sudhakar Katakam
(74) *Attorney, Agent, or Firm* — Hoxie & Associates LLC

(57) ABSTRACT

Provided are novel methods comprising administering a therapeutically effective amount of (1R,5S)-1-(naphthalen-2-yl)-3-azabicyclo[3.1.0]hexane, in free or pharmaceutically acceptable salt form, to a patient in need thereof.

20 Claims, No Drawings

(56) References Cited

OTHER PUBLICATIONS

International Search Report for International Application No. PCT/US2014/069401, dated Mar. 18, 2015, 3 pages.

Micheli, F. et al., "1-(Aryl)-6-[alkoxyalkyl]-3-azabicyclo[3.1.0]hexanes and 6-(Aryl)-6-[alkoxyalkyl]-3-azabicyclo[3.1.0]hexanes: A New Series of Potent and Selective Triple Reuptake Inhibitors," Journal of Medicinal Chemistry, 2010, 53 (6), 2534-2551.

Rueda, J-R. et al., "Systematic Review of Pharmacological Treatments in Fragile X Syndrome," BMC Neurology, 2009, 9, 53, 11 pages, doi:10.1186/1471-2377-9-53.

"Theravance Announces Initiation of Phase 2 Study With Its MARIN Compound, TD-9855, for the Treatment of ADHD," Theravance Press Release, 2 pages, dated 2011, [retrieved on Feb. 17, 2015]. Retrieved from the Internet: <URL: http://www.marketwired.com/press-release/theravance-announces-initiation-phase-2-study-with-its-marin-compound-td-9855-treatment-nasdaq-thrx-1597199.htm>.

Zhang, M. et al., "Studies on the Structure-Activity Relationship of Bicifadine Analogs as Monoamine Transporter Inhibitors," Bioorganic & Medicinal Chemistry Letters, 2008, 18, 3682-3686.

\* cited by examiner

METHODS OF TREATING FRAGILE X ASSOCIATED DISORDERS, ADHD, AND AUTISM SPECTRUM DISORDER

CROSS REFERENCE TO RELATED APPLICATIONS

This application is the National Stage Entry under 35 U.S.C. §371 of International Application No. PCT/US2014/069401 filed Dec. 9, 2014, which claims priority to U.S. Provisional Application No. 61/913,886 filed Dec. 9, 2013, the contents of both of which are hereby incorporated by reference.

BACKGROUND

Fragile X-associated disorders are a family of genetic conditions that may affect individuals in a variety of ways. The three fragile X-associated disorders are fragile X syndrome (FXS), fragile X-associated tremor/ataxia syndrome (FXTAS), and fragile X-associated primary ovarian insufficiency (FXPOI). The conditions are all caused by changes in the fragile X mental retardation 1 (FMR1) gene, located on the X chromosome. In most people, the FMR1 gene contains approximately 5-44 repeats of the cytosine guanine guanine (CGG) trinucleotide within the 5' untranslated region.

Fragile X syndrome (FXS) is the most common inherited form of intellectual disability worldwide. FXS is characterized by an expansion to more than 200 repetitions of the CGG trinucleotide, resulting in loss or significant reduction of expression of the FMR1 gene product, fragile X mental retardation protein (FMRP).

In addition to their intellectual development disability, individuals with FXS may display associated physical features such as large ears, long face, macrocephaly, and macroorchidism. Individuals with FXS may also exhibit one or more of hyperactivity, impulsivity, multiple anxiety symptoms, repetitive/perseverative stereotypic behaviors, unstable affect, aggression, and self-injurious behavior. Males are generally more severely affected than females when carrying the mutation (heterozygous females may appear phenotypically unaffected, but may suffer reproductive abnormalities).

FXTAS is caused by a moderate expansion (55-200 repeats; premutation range) of the CGG trinucleotide in the FMR1 gene. FXTAS is an adult onset neurodegenerative disorder, e.g., occurring over 50 years of age. Affected individuals may exhibit one or more of action tremor, Parkinsonism, sensory neuropathy, cognitive dysfunction (e.g., executive impairment and dementia), anxiety, irritability, agitation, hostility, obsessive-compulsiveness, apathy, and depression.

FXPOI affects women and is also caused by a moderate expansion (55-200 repeats; premutation range) of the CGG trinucleotide in the FMR1 gene. Some women with about 44 to 54 CGG repeats may also have features of FXPOI. Affected women may exhibit intermittent and unpredictable menses, with eventual early cessation. FXPOI may also be associated with late-onset Parkinson-like neurological problems (fragile X-associated tremor ataxia syndrome, or FXTAS) including executive function deficits, tremor, ataxia, neuropathy, and brain atrophy.

In treating fragile X-associated disorders, such as FXS, it has been observed that while available agents may improve some symptoms, they aggravate others.

For instance, stimulants, such as methylphenidate and amphetamines, have been used in individuals with FXS. However, concerns about stimulants include risk of abuse, dependency, and diversion as well as potential neurotoxic effects of amphetamines. In addition, individuals with FXS treated with stimulants have reported increased anxiety, irritability, mood lability, perseveration, hyperactivity, and/or aggressive tendencies.

Selective serotonin reuptake inhibitors (SSRIs), such as sertraline and fluoxetine, have also been used in individuals with FXS. It has been reported, however, that in some individuals, especially children, SSRIs caused behavioral activation (increase in activity level that does not include any real change in mood, impulse control, or a change in the child's demeanor or other behaviors), which can aggravate preexisting symptoms of hyperactivity and disinhibited behaviors.

Aripiprazole has also been tried in individuals with FXS. It has been reported, however, that some individuals with FXS failed treatment predominately due to aggravation of aggressive, perseverative, and irritable behavior.

Atomoxetine, a selective norepinephrine reuptake inhibitor, has also been tried in individuals with FXS. Compared to stimulants, advantages of atomoxetine may include lack of abuse potential and once-daily dosage. Six trials of atomoxetine in individuals with FXS, however, were unsuccessful, with the majority failing due to aggravation of irritable, moody, and aggressive behaviors.

Attention-deficit/hyperactivity disorder (ADHD) and anxiety disorders occur together in 25%-33% of patients. However, as discussed above, concerns about treatment with stimulants include risk of abuse, dependency, and diversion as well as potential neurotoxic effects of amphetamines. In addition, stimulants may exacerbate anxiety.

Accordingly, there remains a need for methods to treat the manifold symptoms associated with a fragile X-associated disorder such as FXS. There also remains a need for methods to treat ADHD co-morbid with anxiety.

BRIEF SUMMARY

Provided is a method of treating a fragile X-associated disorder comprising administering a therapeutically effective amount of (1R,5S)-1-(naphthalen-2-yl)-3-azabicyclo[3.1.0]hexane, in free or pharmaceutically acceptable salt form, to a patient in need thereof.

Further provided is a method of treating attention-deficit/hyperactivity disorder (ADHD) comprising administering a therapeutically effective amount of (1R,5S)-1-(naphthalen-2-yl)-3-azabicyclo[3.1.0]hexane, in free or pharmaceutically acceptable salt form, to a patient in need thereof wherein the patient has a fragile X-associated disorder.

Further provided is a method of treating autism spectrum disorder (ASD) comprising administering a therapeutically effective amount of (1R,5S)-1-(naphthalen-2-yl)-3-azabicyclo[3.1.0]hexane, in free or pharmaceutically acceptable salt form, to a patient in need thereof wherein the patient has a fragile X-associated disorder.

Further provided is a method of treating a fragile X-associated disorder comprising administering a therapeutically effective amount of (1R,5S)-1-(naphthalen-2-yl)-3-azabicyclo[3.1.0]hexane, in free or pharmaceutically acceptable salt form, to a patient in need thereof wherein the patient was refractory to a prior course of treatment for the fragile X-associated disorder.

Further provided is a method of treating attention-deficit/hyperactivity disorder (ADHD) comprising administering a therapeutically effective amount of (1R,5S)-1-(naphthalen-2-yl)-3-azabicyclo[3.1.0]hexane, in free or pharmaceutically acceptable salt form, to a patient in need thereof wherein the ADHD is co-morbid with one or both of anxiety and depression (e.g., depression), e.g., in a patient with a fragile X-associated disorder.

Further areas of applicability of the present disclosure will become apparent from the detailed description provided hereinafter. It should be understood that the detailed description and specific examples, while indicating the preferred embodiment of this disclosure, are intended for purposes of illustration only and are not intended to limit the scope of this disclosure.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

(1R,5S)-1-(naphthalen-2-yl)-3-azabicyclo[3.1.0]hexane, also known as (+)-1-(naphthalen-2-yl)-3-azabicyclo[3.1.0]hexane, is shown as Formula I below.

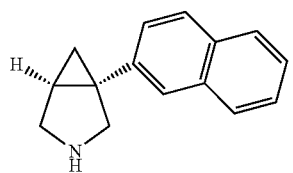

Formula I

"(1R,5S)-1-(naphthalen-2-yl)-3-azabicyclo[3.1.0]hexane" and "(+)-1-(naphthalen-2-yl)-3-azabicyclo[3.1.0]hexane" are used interchangeably herein.

(1R,5S)-1-(naphthalen-2-yl)-3-azabicyclo[3.1.0]hexane is an unbalanced triple reuptake inhibitor with the most potency towards norepinephrine reuptake (NE), one-sixth as much towards dopamine reuptake (DA), and one-fourteenth as much towards serotonin reuptake (5-HT).

Although individuals with a fragile X-associated disorder, such as FXS, may exhibit symptoms similar to ADHD, their response to treatment is somewhat different. Thus, while stimulants have been used in individuals with FXS, such treatment may not be optimal because of the sensitivity of individuals with FXS to dopaminergic medications. For instance, individuals with FXS treated with stimulants have shown increased anxiety, irritability, mood lability, perseveration, hyperactivity, and/or aggressive tendencies. Stimulants also have substance abuse concerns.

Meanwhile a drug with minimal to no effect on dopamine may not provide optimal treatment for FXS either. For instance, six trials of atomoxetine, a selective norepinephrine reuptake inhibitor, in individuals with FXS, were unsuccessful, with the majority failing due to aggravation of irritable, moody, and aggressive behaviors.

Compared to atomoxetine, (1R,5S)-1-(naphthalen-2-yl)-3-azabicyclo[3.1.0]hexane also enhances dopamine function, but without the pronounced dopaminergic activities of stimulants. Thus, in individuals with FXS, the unbalanced norepinephrine-dopamine-serotonin reuptake inhibition profile of (1R,5S)-1-(naphthalen-2-yl)-3-azabicyclo[3.1.0]hexane may affect the norepinephrine, dopamine, and serotonin circuitries without causing the increased anxiety, irritability, mood lability, perseveration, hyperactivity, and/or aggressive tendencies that have been seen with stimulants in individuals with FXS and without triggering substance abuse associated with dopamine seen with stimulants. In addition, the multi-functional effects of (1R,5S)-1-(naphthalen-2-yl)-3-azabicyclo[3.1.0]hexane may be useful in treating the manifold symptoms associated with a fragile X-associated disorder such as FXS. Further, affecting the norepinephrine, dopamine, and serotonin circuitries with one drug may avoid pharmacologic drug-drug interactions (DDIs). For instance, administering two drugs with different effects on the norepinephrine, dopamine, and/or serotonin circuitries may result in off-target interactions potentially leading to undesirable and unexpected changes in norepinephrine, dopamine, and/or serotonin levels.

It has been reported that cytochrome P450 enzyme isoforms (CYPs), which catalyze oxidative reactions, account for the metabolism of 75% of all drugs, and in particular, about 80% of drugs cleared by CYPs are metabolized by four CYP isoforms—CYP3A4, CYP2D6, CYP2C9 and CYP2C19. Thus, these four CYPs are potential candidates for DDIs. Physicians consider potential DDIs and metabolic pathway(s) when selecting treatments. (1R,5S)-1-(naphthalen-2-yl)-3-azabicyclo[3.1.0]hexane is primarily metabolized by monoamine oxidase A (MAO A) which may spare the liver and may reduce drug-drug interactions if (1R,5S)-1-(naphthalen-2-yl)-3-azabicyclo[3.1.0]hexane is used in a combination therapy, e.g., with a drug that is metabolized by CYPs, e.g., mavoglurant.

In individuals having ADHD with co-morbid anxiety, stimulants may exacerbate anxiety. In addition, administering two drugs with different effects on the norepinephrine, dopamine, and/or serotonin circuitries may result in off-target interactions potentially leading to undesirable and unexpected changes in norepinephrine, dopamine, and/or serotonin levels.

(1R,5S)-1-(naphthalen-2-yl)-3-azabicyclo[3.1.0]hexane enhances dopamine function, but without the pronounced dopaminergic activities of stimulants. In addition, the multi-functional effects of (1R,5S)-1-(naphthalen-2-yl)-3-azabicyclo[3.1.0]hexane may be useful in treating ADHD with co-morbid anxiety. Further, affecting the norepinephrine, dopamine, and serotonin circuitries with one drug may avoid pharmacologic drug-drug interactions (DDIs).

(1R,5S)-1-(naphthalen-2-yl)-3-azabicyclo[3.1.0]hexane may be synthesized as described in U.S. Pat. No. 8,461,196 or International Publication No. WO 2013/019271, both of which are incorporated herein by reference in their entirety.

As used herein, "substantially free of the corresponding (−) enantiomer" means more of (1R,5S)-1-(naphthalen-2-yl)-3-azabicyclo[3.1.0]hexane than the corresponding (−) enantiomer, i.e., (1S,5R)-1-(naphthalen-2-yl)-3-azabicyclo[3.1.0]hexane. In some embodiments, "substantially free of the corresponding (−) enantiomer" means containing no more than 20% w/w (weight/weight) of the corresponding (−) enantiomer, in free or pharmaceutically acceptable salt form, e.g., no more than 10% w/w of the corresponding (−) enantiomer, in free or pharmaceutically acceptable salt form, e.g., no more than 5% w/w of the corresponding (−) enantiomer, in free or pharmaceutically acceptable salt form, e.g., no more than 2% w/w of the corresponding (−) enantiomer, in free or pharmaceutically acceptable salt form, e.g., no more than 1% w/w of the corresponding (−) enantiomer, in free or pharmaceutically acceptable salt form.

As used herein, "(1R,5S)-1-(naphthalen-2-yl)-3-azabicyclo[3.1.0]hexane" embraces the compound in any form, for example, free or pharmaceutically acceptable salt form, e.g., as a pharmaceutically acceptable acid addition salt. Pharmaceutically acceptable salts are known in the art and include salts that are physiologically acceptable at the dosage amount and form to be administered, for example, hydrochloride salts.

As used herein, "(1R,5S)-1-(naphthalen-2-yl)-3-azabicyclo[3.1.0]hexane" is also to be understood as embracing the compound in crystalline and amorphous form including, for example, polymorphs, solvates (including hydrates), unsolvated polymorphs (including anhydrates), conformational polymorphs, and amorphous forms of the compounds, as well as mixtures thereof "Crystalline form" and "polymorph" may be used interchangeably herein, and are meant to include all crystalline forms of (1R,5S)-1-(naphthalen-2-yl)-3-azabicyclo[3.1.0]hexane, in free or pharmaceutically acceptable salt form, including, for example, polymorphs, solvates (including hydrates), unsolvated polymorphs (including anhydrates), and conformational polymorphs, as well as mixtures thereof, unless a particular crystalline form is referred to.

Crystalline and amorphous forms of (1R,5S)-1-(naphthalen-2-yl)-3-azabicyclo[3.1.0]hexane may be used in any combination or in forms that are substantially free of one or more of the other crystalline forms or free of the amorphous form.

As used herein, "substantially free of other polymorphic forms" means that the crystalline material contains no more than 10% w/w of any other crystalline form, e.g., no more than 5% w/w of any other crystalline form, no more than 2% w/w of any other crystalline form, e.g., no more than 1% w/w of any other crystalline form.

(1R,5S)-1-(naphthalen-2-yl)-3-azabicyclo[3.1.0]hexane may in some cases also exist in prodrug form. Prodrugs are considered to be any covalently bonded carriers that release the active parent drug in vivo.

As used herein, the term "patient" includes human or non-human (i.e., animal) patient. In some embodiments, patient encompasses both human and nonhuman. In some embodiments, patient means a nonhuman. In other embodiments, patient means a human.

As used herein, "therapeutically effective amount" refers to an amount effective, when administered to a human or non-human patient, to provide a therapeutic benefit such as amelioration of symptoms. The specific dose of substance administered to obtain a therapeutic benefit will, of course, be determined by the particular circumstances surrounding the case, including, for example, the specific substance administered, the route of administration, the condition being treated, and the individual being treated.

As used herein, "concurrently" means the compounds are administered simultaneously or within the same composition. In some embodiments, the compounds are administered simultaneously. In some embodiments, the compounds are administered within the same composition.

As used herein, "autism spectrum disorder," includes autistic disorder (classic autism), Asperger's disorder (Asperger syndrome), pervasive developmental disorder not otherwise specified (PDD-NOS), Rett's disorder (Rett syndrome), and childhood disintegrative disorder (CDD).

As used herein, "a patient that was refractory to a prior course of treatment for a fragile-X associated disorder" refers to a patient who has previously been treated one or more times for a fragile-X associated disorder, i.e., a patient that has not responded to a prior course of treatment, that responded in an unsatisfactory manner to a prior course of treatment, that was unable to tolerate a prior course of treatment, and/or that otherwise responded in an unsatisfactory manner to a prior course of treatment. A prior course of treatment may include, but is not limited to, an anti-depressant (e.g., a selective serotonin reuptake inhibitor), a stimulant, and/or an antipsychotic (e.g., a typical and/or atypical antipsychotic). A patient that was refractory to a prior course of treatment for a fragile-X associated disorder may have been refractory for any reason. In some embodiments, a patient that was refractory to a prior course of treatment for a fragile-X associated disorder may have failed to respond or failed to respond sufficiently to a prior course of treatment for the fragile-X associated disorder. In other embodiments, a patient that was refractory to a prior course of treatment for a fragile-X associated disorder may have initially responded to treatment. In some embodiments, a patient that was refractory to a prior course of treatment for a fragile-X associated disorder may have been unable to continue taking the prior course of treatment due to intolerance of the prior course of treatment because of side effects including, but not limited to, increased anxiety, irritability, mood lability, perseveration, hyperactivity, aggressive tendencies, and/or disinhibited behaviors and/or sexual dysfunction, weight gain, insomnia, dry mouth, constipation, nausea and vomiting, dizziness, memory loss, agitation, anxiety, sedation, headache, urinary retention, and/or abdominal pain. An unsatisfactory or failed response may be determined by any means generally used, including patient self-reporting and/or clinical observation.

ADHD includes three sub-types: predominantly inattentive type, predominantly hyperactive-impulsive type, and combined type.

Anxiety may be characterized by feelings of tension and worried thoughts. Anxiety disorders may cause recurring intrusive thoughts or concerns. Anxiety disorders include generalized anxiety disorder, panic disorder, social anxiety disorder, obsessive-compulsive disorder, phobias, and post-traumatic stress disorder.

Provided is a method (Method 1) of treating a patient having a fragile X-associated disorder comprising administering to the patient in need thereof a therapeutically effective amount of (1R,5S)-1-(naphthalen-2-yl)-3-azabicyclo[3.1.0]hexane, in free or pharmaceutically acceptable salt form.

Further provided is Method 1 as follows:
1.1 Method 1 wherein the therapeutically effective amount of (1R,5S)-1-(naphthalen-2-yl)-3-azabicyclo[3.1.0]hexane, in free or pharmaceutically acceptable salt form, is substantially free of the corresponding (−) enantiomer.
1.2 Method 1 or 1.1 wherein the therapeutically effective amount of (1R,5S)-1-(naphthalen-2-yl)-3-azabicyclo[3.1.0]hexane, in free or pharmaceutically acceptable salt form, comprises less than or equal to 20% w/w of the corresponding (−) enantiomer.
1.3 Method 1, 1.1, or 1.2 wherein the therapeutically effective amount of (1R,5S)-1-(naphthalen-2-yl)-3-azabicyclo[3.1.0]hexane, in free or pharmaceutically acceptable salt form, comprises less than or equal to 10% w/w of the corresponding (−) enantiomer.
1.4 Any of Methods 1 or 1.1-1.3 wherein the therapeutically effective amount of (1R,5S)-1-(naphthalen-2-yl)-3-azabicyclo[3.1.0]hexane, in free or pharmaceutically acceptable salt form, comprises less than or equal to 5% w/w of the corresponding (−) enantiomer.

1.5 Any of Methods 1 or 1.1-1.4 wherein the therapeutically effective amount of (1R,5S)-1-(naphthalen-2-yl)-3-azabicyclo[3.1.0]hexane, in free or pharmaceutically acceptable salt form, comprises less than or equal to 2% w/w of the corresponding (−) enantiomer.

1.6 Any of Methods 1 or 1.1-1.5 wherein the therapeutically effective amount of (1R,5S)-1-(naphthalen-2-yl)-3-azabicyclo[3.1.0]hexane, in free or pharmaceutically acceptable salt form, comprises less than or equal to 1% w/w of the corresponding (−) enantiomer.

1.7 Any of Methods 1 or 1.1-1.6 wherein (1R,5S)-1-(naphthalen-2-yl)-3-azabicyclo[3.1.0]hexane is in pharmaceutically acceptable salt form.

1.8 Method 1.7 wherein (1R,5S)-1-(naphthalen-2-yl)-3-azabicyclo[3.1.0]hexane in pharmaceutically acceptable salt form is an acid addition salt.

1.9 Method 1.8 wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo[3.1.0]hexane hydrochloride.

1.10 Any of Methods 1 or 1.1-1.9 wherein (1R,5S)-1-(naphthalen-2-yl)-3-azabicyclo[3.1.0]hexane, in free or pharmaceutically acceptable salt form, is crystalline.

1.11 Any of Methods 1 or 1.1-1.10 comprising administering 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of (1R,5S)-1-(naphthalen-2-yl)-3-azabicyclo[3.1.0]hexane, in free or pharmaceutically acceptable salt form.

1.12 Any of Methods 1 or 1.1-1.11 comprising administering 75 mg to 1000 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

1.13 Any of Methods 1 or 1.1-1.11 comprising administering 50 mg to 600 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

1.14 Any of Methods 1 or 1.1-1.11 comprising administering 5 mg to 500 mg, e.g., 5 mg to 10 mg, e.g, 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of (1R,5S)-1-(naphthalen-2-yl)-3-azabicyclo[3.1.0]hexane, in free or pharmaceutically acceptable salt form.

1.15 Any of Methods 1 or 1.1-1.10 comprising administering 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of (1R,5S)-1-(naphthalen-2-yl)-3-azabicyclo[3.1.0]hexane, in free or pharmaceutically acceptable salt form.

1.16 Any of Methods 1 or 1.1-1.15 comprising administering (1R,5S)-1-(naphthalen-2-yl)-3-azabicyclo[3.1.0]hexane, in free or pharmaceutically acceptable salt form, once, twice, three, or four times daily.

1.17 Any of Methods 1 or 1.1-1.16 comprising administering (1R,5S)-1-(naphthalen-2-yl)-3-azabicyclo[3.1.0]hexane, in free or pharmaceutically acceptable salt form, once daily.

1.18 Any of Methods 1 or 1.1-1.17 comprising administering (1R,5S)-1-(naphthalen-2-yl)-3-azabicyclo[3.1.0]hexane, in free or pharmaceutically acceptable salt form, twice daily.

1.19 Any of Methods 1 or 1.1-1.18 comprising administering (1R,5S)-1-(naphthalen-2-yl)-3-azabicyclo[3.1.0]hexane, in free or pharmaceutically acceptable salt form, three times daily.

1.20 Any of Methods 1 or 1.1-1.19 comprising administering (1R,5S)-1-(naphthalen-2-yl)-3-azabicyclo[3.1.0]hexane, in free or pharmaceutically acceptable salt form, four times daily.

1.21 Any of Methods 1 or 1.1-1.20 wherein (1R,5S)-1-(naphthalen-2-yl)-3-azabicyclo[3.1.0]hexane, in free or pharmaceutically acceptable salt form, is administered concurrently or sequentially, in either order, with another drug.

1.22 Any of Methods 1 or 1.1-1.21 wherein (1R,5S)-1-(naphthalen-2-yl)-3-azabicyclo[3.1.0]hexane, in free or pharmaceutically acceptable salt form, is administered concurrently or sequentially, in either order, with an mGluR1 antagonist, an mGluR2/3 antagonist, an mGluR5 antagonist, an AMPA receptor positive modulator, an NMDA receptor antagonist, a tetracycline antibiotic, an α2-adrenergic agonist, an antipsychotic, an anti-depressant (e.g., a selective serotonin reuptake inhibitor (SSRI), a serotonin-norepinephrine reuptake inhibitor (SNRI), or a tricyclic anti-depressant), a benzodiazepine, an anti-convulsant, a mood stabilizer, a gamma-aminobutyric acid (GABA) agonist e.g., a GABA-B agonist, a GABA modulator, a stimulant, a β-blocker, a hormone, or a combination thereof 1.23 Any of Methods 1 or 1.1-1.22 wherein (1R,5S)-1-(naphthalen-2-yl)-3-azabicyclo[3.1.0]hexane, in free or pharmaceutically acceptable salt form, is administered concurrently or sequentially, in either order, with fenobam, mavoglurant (AFQ056), dipraglurant, RO4917523, STX107, 2-methyl-6-phenylethynyl pyridine (MPEP), CX516, memantine, acamprosate, minocycline, clonidine, guanfacine, aripiprazole, risperidone, citalopram, escitalopram, fluoxetine, sertraline, fluvoxamine, paroxetine, trazodone, bupropion, imipramine, amitriptyline, venlafaxine, nefazodone, duloxetine, venlafaxine, carbamazepine, lamotrigine, valproic acid, sodium valproate, lithium, quetiapine, folic acid, L-acetylcarnitine, melatonin, arbaclofen, donepezil hydrochloride, alpha-tocopherol, methylphenidate, amphetamine mixed salts (e.g., Adderall), dextroamphetamine, risperidone, olanzapine, ziprasidone, buspirone, filuzole, metadoxine, primidone, topiramate, estradiol, cyclic medroxyprogesterone, or a combination thereof 1.24 Any of Methods 1 or 1.1-1.23 further comprising administering an mGluR5 antagonist.

1.25 Method 1.24 comprising administering fenobam, mavoglurant (AFQ056), dipraglurant, RO4917523, STX107, 2-methyl-6-phenylethynyl pyridine (MPEP), or a combination thereof 1.26 Method 1.25 comprising administering RO4917523, mavoglurant (AFQ056), or a combination thereof 1.27 Any of Methods 1 or 1.1-1.26 further comprising administering a GABA-B agonist.

1.28 Method 1.27 comprising administering arbaclofen.

1.29 Any of Methods 1 or 1.1-1.28 further comprising administering a GABA modulator.

1.30 Method 1.29 comprising administering acamprosate.

1.31 Any of Methods 1 or 1.1-1.30 further comprising administering minocycline.

1.32 Any of Methods 1 or 1.1-1.31 further comprising a non-pharmacological intervention, e.g., a modification in the home environment, a more tailored behavioral intervention and classroom environment, language and occupational therapy, an attention to social factors, sensory integration therapy, or a combination thereof 1.33 Any of Methods 1 or 1.1-1.32 wherein the (1R,5S)-1-(naphthalen-2-yl)-3-azabicyclo[3.1.0]hexane, in free or pharmaceutically acceptable salt form, is administered in a sustained release pharmaceutical composition.

1.34 Method 1.33 wherein the $C_{max}$ of (1R,5S)-1-(naphthalen-2-yl)-3-azabicyclo[3.1.0]hexane, in free or pharmaceutically acceptable salt form, provided after administration of the sustained release pharmaceutical composition is less than about 80%, e.g., less than about 75%, e.g., less than about 60%, e.g., less than about 50%, e.g., less than about 40%, e.g., less than about 30%, e.g., is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

1.35 Method 1.34 wherein the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, e.g., is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

1.36 Any of Methods 1 or 1.1-1.35 wherein the fragile X-associated disorder is fragile X syndrome (FXS).

1.37 Any of Methods 1 or 1.1-1.35 wherein the fragile X-associated disorder is fragile X-associated tremor/ataxia syndrome (FXTAS).

1.38 Any of Methods 1 or 1.1-1.35 wherein the fragile X-associated disorder is fragile X-associated primary ovarian insufficiency (FXPOI).

1.39 Any of Methods 1 or 1.1-1.35 wherein the fragile X-associated disorder is associated with an expansion to 40, e.g., 44 or more, e.g., 50 or more, e.g., 54 or more, e.g., 80 or more, e.g, 100 or more, e.g., 200 or more repeats, of the cytosine guanine guanine (CGG) trinucleotide within the 5' untranslated region of the FMR1 gene located on the X chromosome.

1.40 Any of Methods 1 or 1.1-1.39 wherein the treatment improves one or more symptoms associated with the fragile X-associated disorder.

1.41 Method 1.40 wherein the one or more symptoms comprise one or more of cognitive impairment, anxiety, hyperactivity, impulsivity, repetitive/perseverative stereotypic behaviors, unstable affect, aggression, and self-injurious behavior.

Also provided is use of (1R,5S)-1-(naphthalen-2-yl)-3-azabicyclo[3.1.0]hexane, in free or pharmaceutically acceptable salt form, in the manufacture of a medicament for treating a patient having a fragile X-associated disorder, e.g., for use in Method 1, e.g., Methods 1.1-1.41.

Also provided is a pharmaceutical composition comprising (1R,5S)-1-(naphthalen-2-yl)-3-azabicyclo[3.1.0]hexane, in free or pharmaceutically acceptable salt form, in combination with a pharmaceutically acceptable diluent or carrier for use in treating a patient having a fragile X-associated disorder, e.g., for use in Method 1, e.g., Methods 1.1-1.41.

Also provided is a method (Method 2) of treating attention-deficit/hyperactivity disorder (ADHD) comprising administering a therapeutically effective amount of (1R,5S)-1-(naphthalen-2-yl)-3-azabicyclo[3.1.0]hexane, in free or pharmaceutically acceptable salt form, to a patient in need thereof wherein the patient has a fragile X-associated disorder.

Further provided is Method 2 as follows:

2.1 Method 2 wherein the therapeutically effective amount of (1R,5S)-1-(naphthalen-2-yl)-3-azabicyclo[3.1.0]hexane, in free or pharmaceutically acceptable salt form, is substantially free of the corresponding (−) enantiomer.

2.2 Method 2 or 2.1 wherein the therapeutically effective amount of (1R,5S)-1-(naphthalen-2-yl)-3-azabicyclo[3.1.0]hexane, in free or pharmaceutically acceptable salt form, comprises less than or equal to 20% w/w of the corresponding (−) enantiomer.

2.3 Method 2, 2.1, or 2.2 wherein the therapeutically effective amount of (1R,5S)-1-(naphthalen-2-yl)-3-azabicyclo[3.1.0]hexane, in free or pharmaceutically acceptable salt form, comprises less than or equal to 10% w/w of the corresponding (−) enantiomer.

2.4 Any of Methods 2 or 2.1-2.3 wherein the therapeutically effective amount of (1R,5S)-1-(naphthalen-2-yl)-3-azabicyclo[3.1.0]hexane, in free or pharmaceutically acceptable salt form, comprises less than or equal to 5% w/w of the corresponding (−) enantiomer.

2.5 Any of Methods 2 or 2.1-2.4 wherein the therapeutically effective amount of (1R,5S)-1-(naphthalen-2-yl)-3-azabicyclo[3.1.0]hexane, in free or pharmaceutically acceptable salt form, comprises less than or equal to 2% w/w of the corresponding (−) enantiomer.

2.6 Any of Methods 2 or 2.1-2.5 wherein the therapeutically effective amount of (1R,5S)-1-(naphthalen-2-yl)-3-azabicyclo[3.1.0]hexane, in free or pharmaceutically acceptable salt form, comprises less than or equal to 1% w/w of the corresponding (−) enantiomer.

2.7 Any of Methods 2 or 2.1-2.6 wherein (1R,5S)-1-(naphthalen-2-yl)-3-azabicyclo[3.1.0]hexane is in pharmaceutically acceptable salt form.

2.8 Method 2.7 wherein (1R,5S)-1-(naphthalen-2-yl)-3-azabicyclo[3.1.0]hexane in pharmaceutically acceptable salt form is an acid addition salt.

2.9 Method 2.8 wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo[3.1.0]hexane hydrochloride.

2.10 Any of Methods 2 or 2.1-2.9 wherein (1R,5S)-1-(naphthalen-2-yl)-3-azabicyclo[3.1.0]hexane, in free or pharmaceutically acceptable salt form, is crystalline.

2.11 Any of Methods 2 or 2.1-2.10 comprising administering 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of (1R,5S)-1-(naphthalen-2-yl)-3-azabicyclo[3.1.0]hexane, in free or pharmaceutically acceptable salt form.

2.12 Any of Methods 2 or 2.1-2.11 comprising administering 75 mg to 1000 mg, e.g., 100 mg to 600 mg, e.g., 100 mg to 400 mg, e.g., 100 mg to 200 mg, of (1R,5S)-1-

2.13 Any of Methods 2 or 2.1-2.11 comprising administering 50 mg to 600 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

2.14 Any of Methods 2 or 2.1-2.11 comprising administering 5 mg to 500 mg, e.g., 5 mg to 10 mg, e.g., 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of (1R,5S)-1-(naphthalen-2-yl)-3-azabicyclo[3.1.0]hexane, in free or pharmaceutically acceptable salt form.

2.15 Any of Methods 2 or 2.1-2.10 comprising administering 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of (1R,5S)-1-(naphthalen-2-yl)-3-azabicyclo[3.1.0]hexane, in free or pharmaceutically acceptable salt form.

2.16 Any of Methods 2 or 2.1-2.15 comprising administering (1R,5S)-1-(naphthalen-2-yl)-3-azabicyclo[3.1.0]hexane, in free or pharmaceutically acceptable salt form, once, twice, three, or four times daily.

2.17 Any of Methods 2 or 2.1-2.16 comprising administering (1R,5S)-1-(naphthalen-2-yl)-3-azabicyclo[3.1.0]hexane, in free or pharmaceutically acceptable salt form, once daily.

2.18 Any of Methods 2 or 2.1-2.17 comprising administering (1R,5S)-1-(naphthalen-2-yl)-3-azabicyclo[3.1.0]hexane, in free or pharmaceutically acceptable salt form, twice daily.

2.19 Any of Methods 2 or 2.1-2.18 comprising administering (1R,5S)-1-(naphthalen-2-yl)-3-azabicyclo[3.1.0]hexane, in free or pharmaceutically acceptable salt form, three times daily.

2.20 Any of Methods 2 or 2.1-2.19 comprising administering (1R,5S)-1-(naphthalen-2-yl)-3-azabicyclo[3.1.0]hexane, in free or pharmaceutically acceptable salt form, four times daily.

2.21 Any of Methods 2 or 2.1-2.20 wherein (1R,5S)-1-(naphthalen-2-yl)-3-azabicyclo[3.1.0]hexane, in free or pharmaceutically acceptable salt form, is administered concurrently or sequentially, in either order, with another drug.

2.22 Any of Methods 2 or 2.1-2.21 wherein (1R,5S)-1-(naphthalen-2-yl)-3-azabicyclo[3.1.0]hexane, in free or pharmaceutically acceptable salt form, is administered concurrently or sequentially, in either order, with an mGluR1 antagonist, an mGluR2/3 antagonist, an mGluR5 antagonist, an AMPA receptor positive modulator, an NMDA receptor antagonist, a tetracycline antibiotic, an α2-adrenergic agonist, an antipsychotic, an anti-depressant (e.g., a selective serotonin reuptake inhibitor (SSRI), a serotonin-norepinephrine reuptake inhibitor (SNRI), or a tricyclic anti-depressant), a benzodiazepine, an anticonvulsant, a mood stabilizer, a gamma-aminobutyric acid (GABA) agonist e.g., a GABA-B agonist, a GABA modulator, a stimulant, a β-blocker, a hormone, or a combination thereof 2.23 Any of Methods 2 or 2.1-2.22 wherein (1R,5S)-1-(naphthalen-2-yl)-3-azabicyclo[3.1.0]hexane, in free or pharmaceutically acceptable salt form, is administered concurrently or sequentially, in either order, with fenobam, mavoglurant (AFQ056), dipraglurant, RO4917523, STX107, 2-methyl-6-phenylethynyl pyridine (MPEP), CX516, memantine, acamprosate, minocycline, clonidine, guanfacine, aripiprazole, risperidone, citalopram, escitalopram, fluoxetine, sertraline, fluovoxamine, paroxetine, trazodone, bupropion, imipramine, amitriptyline, venlafaxine, nefazodone, duloxetine, venlafaxine, carbamazepine, lamotrigine, valproic acid, sodium valproate, lithium, quetiapine, folic acid, L-acetylcarnitine, melatonin, arbaclofen, donepezil hydrochloride, alpha-tocopherol, methylphenidate, amphetamine mixed salts (e.g., Adderall), dextroamphetamine, risperidone, olanzapine, ziprasidone, buspirone, filuzole, metadoxine, primidone, topiramate, estradiol, cyclic medroxyprogesterone, or a combination thereof.

2.24 Any of Methods 2 or 2.1-2.23 further comprising administering an mGluR5 antagonist.

2.25 Method 2.24 comprising administering fenobam, mavoglurant (AFQ056), dipraglurant, RO4917523, STX107, 2-methyl-6-phenylethynyl pyridine (MPEP), or a combination thereof 2.26 Method 2.25 comprising administering RO4917523, mavoglurant (AFQ056), or a combination thereof 2.27 Any of Methods 2 or 2.1-2.26 further comprising administering a GABA-B agonist.

2.28 Method 2.27 comprising administering arbaclofen.

2.29 Any of Methods 2 or 2.1-2.28 further comprising administering a GABA modulator.

2.30 Method 2.29 comprising administering acamprosate.

2.31 Any of methods 2 or 2.1-2.30 further comprising administering minocycline.

2.32 Any of Methods 2 or 2.1-2.31 further comprising a non-pharmacological intervention, e.g., a modification in the home environment, a more tailored behavioral intervention and classroom environment, language and occupational therapy, an attention to social factors, sensory integration therapy, or a combination thereof 2.33 Any of Methods 2 or 2.1-2.32 wherein the (1R,5S)-1-(naphthalen-2-yl)-3-azabicyclo[3.1.0]hexane, in free or pharmaceutically acceptable salt form, is administered in a sustained release pharmaceutical composition.

2.34 Method 2.33 wherein the $C_{max}$ of (1R,5S)-1-(naphthalen-2-yl)-3-azabicyclo[3.1.0]hexane, in free or pharmaceutically acceptable salt form, provided after administration of the sustained release pharmaceutical composition is less than about 80%, e.g., less than about 75%, e.g., less than about 60%, e.g., less than about 50%, e.g., less than about 40%, e.g., less than about 30%, e.g., is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

2.35 Method 2.34 wherein the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, e.g., is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

2.36 Any of Methods 2 or 2.1-2.35 wherein the fragile X-associated disorder is fragile X syndrome (FXS).

2.37 Any of Methods 2 or 2.1-2.35 wherein the fragile X-associated disorder is fragile X-associated tremor/ataxia syndrome (FXTAS).

2.38 Any of Methods 2 or 2.1-2.35 wherein the fragile X-associated disorder is fragile X-associated primary ovarian insufficiency (FXPOI).

2.39 Any of Methods 2 or 2.1-2.35 wherein the fragile X-associated disorder is associated with an expansion to 40, e.g., 44 or more, e.g., 50 or more, e.g., 54 or more, e.g., 80 or more, e.g., 100 or more, e.g., 200 or more repeats, of the cytosine guanine guanine (CGG) trinucleotide within the 5' untranslated region of the FMR1 gene located on the X chromosome.

Also provided is use of (1R,5S)-1-(naphthalen-2-yl)-3-azabicyclo[3.1.0]hexane, in free or pharmaceutically acceptable salt form, in the manufacture of a medicament for treating attention-deficit/hyperactivity disorder (ADHD) in a patient in need thereof, wherein the patient has a fragile X-associated disorder, e.g., for use in Method 2, e.g., Methods 2.1-2.39.

Also provided is a pharmaceutical composition comprising (1R,5S)-1-(naphthalen-2-yl)-3-azabicyclo[3.1.0]hexane, in free or pharmaceutically acceptable salt form, in combination with a pharmaceutically acceptable diluent or carrier for use in treating attention-deficit/hyperactivity disorder (ADHD) in a patient in need thereof, wherein the patient has a fragile X-associated disorder, e.g., for use in Method 2, e.g., Methods 2.1-2.39.

Also provided is a method (Method 3) of treating autism spectrum disorder (ASD) comprising administering a therapeutically effective amount of (1R,5S)-1-(naphthalen-2-yl)-3-azabicyclo[3.1.0]hexane, in free or pharmaceutically acceptable salt form, to a patient in need thereof wherein the patient has a fragile X-associated disorder.

Further provided is Method 3 as follows:

3.1 Method 3 wherein the therapeutically effective amount of (1R,5S)-1-(naphthalen-2-yl)-3-azabicyclo[3.1.0] hexane, in free or pharmaceutically acceptable salt form, is substantially free of the corresponding (−) enantiomer.

3.2 Method 3 or 3.1 wherein the therapeutically effective amount of (1R,5S)-1-(naphthalen-2-yl)-3-azabicyclo [3.1.0]hexane, in free or pharmaceutically acceptable salt form, comprises less than or equal to 20% w/w of the corresponding (−) enantiomer.

3.3 Method 3, 3.1, or 3.2 wherein the therapeutically effective amount of (1R,5S)-1-(naphthalen-2-yl)-3-azabicyclo [3.1.0]hexane, in free or pharmaceutically acceptable salt form, comprises less than or equal to 10% w/w of the corresponding (−) enantiomer.

3.4 Any of Methods 3 or 3.1-3.3 wherein the therapeutically effective amount of (1R,5S)-1-(naphthalen-2-yl)-3-azabicyclo[3.1.0]hexane, in free or pharmaceutically acceptable salt form, comprises less than or equal to 5% w/w of the corresponding (−) enantiomer.

3.5 Any of Methods 3 or 3.1-3.4 wherein the therapeutically effective amount of (1R,5S)-1-(naphthalen-2-yl)-3-azabicyclo[3.1.0]hexane, in free or pharmaceutically acceptable salt form, comprises less than or equal to 2% w/w of the corresponding (−) enantiomer.

3.6 Any of Methods 3 or 3.1-3.5 wherein the therapeutically effective amount of (1R,5S)-1-(naphthalen-2-yl)-3-azabicyclo[3.1.0]hexane, in free or pharmaceutically acceptable salt form, comprises less than or equal to 1% w/w of the corresponding (−) enantiomer.

3.7 Any of Methods 3 or 3.1-3.6 wherein (1R,5S)-1-(naphthalen-2-yl)-3-azabicyclo[3.1.0]hexane is in pharmaceutically acceptable salt form.

3.8 Method 3.7 wherein (1R,5S)-1-(naphthalen-2-yl)-3-azabicyclo[3.1.0]hexane in pharmaceutically acceptable salt form is an acid addition salt.

3.9 Method 3.8 wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo [3.1.0]hexane hydrochloride.

3.10 Any of Methods 3 or 3.1-3.9 wherein (1R,5S)-1-(naphthalen-2-yl)-3-azabicyclo[3.1.0]hexane, in free or pharmaceutically acceptable salt form, is crystalline.

3.11 Any of Methods 3 or 3.1-3.10 comprising administering 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of (1R,5S)-1-(naphthalen-2-yl)-3-azabicyclo [3.1.0]hexane, in free or pharmaceutically acceptable salt form.

3.12 Any of Methods 3 or 3.1-3.11 comprising administering 75 mg to 1000 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

3.13 Any of Methods 3 or 3.1-3.11 comprising administering 50 mg to 600 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

3.14 Any of Methods 3 or 3.1-3.11 comprising administering 5 mg to 500 mg, e.g., 5 mg to 10 mg, e.g, 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of (1R,5S)-1-(naphthalen-2-yl)-3-azabicyclo[3.1.0]hexane, in free or pharmaceutically acceptable salt form.

3.15 Any of Methods 3 or 3.1-3.10 comprising administering 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of (1R,5S)-1-(naphthalen-2-yl)-3-azabicyclo[3.1.0]hexane, in free or pharmaceutically acceptable salt form.

3.16 Any of Methods 3 or 3.1-3.15 comprising administering (1R,5S)-1-(naphthalen-2-yl)-3-azabicyclo[3.1.0] hexane, in free or pharmaceutically acceptable salt form, once, twice, three, or four times daily.

3.17 Any of Methods 3 or 3.1-3.16 comprising administering (1R,5S)-1-(naphthalen-2-yl)-3-azabicyclo[3.1.0] hexane, in free or pharmaceutically acceptable salt form, once daily.

3.18 Any of Methods 3 or 3.1-3.17 comprising administering (1R,5S)-1-(naphthalen-2-yl)-3-azabicyclo[3.1.0] hexane, in free or pharmaceutically acceptable salt form, twice daily.

3.19 Any of Methods 3 or 3.1-3.18 comprising administering (1R,5S)-1-(naphthalen-2-yl)-3-azabicyclo[3.1.0] hexane, in free or pharmaceutically acceptable salt form, three times daily.

3.20 Any of Methods 3 or 3.1-3.19 comprising administering (1R,5S)-1-(naphthalen-2-yl)-3-azabicyclo[3.1.0] hexane, in free or pharmaceutically acceptable salt form, four times daily.

3.21 Any of Methods 3 or 3.1-3.20 wherein (1R,5S)-1-(naphthalen-2-yl)-3-azabicyclo[3.1.0]hexane, in free or pharmaceutically acceptable salt form, is administered concurrently or sequentially, in either order, with another drug.

3.22 Any of Methods 3 or 3.1-3.21 wherein (1R,5S)-1-(naphthalen-2-yl)-3-azabicyclo[3.1.0]hexane, in free or pharmaceutically acceptable salt form, is administered concurrently or sequentially, in either order, with an mGluR1 antagonist, an mGluR2/3 antagonist, an mGluR5 antagonist, an AMPA receptor positive modulator, an NMDA receptor antagonist, a tetracycline antibiotic, an α2-adrenergic agonist, an antipsychotic, an anti-depressant (e.g., a selective serotonin reuptake inhibitor (SSRI), a serotonin-norepinephrine reuptake inhibitor (SNRI), or a tricyclic anti-depressant), a benzodiazepine, an anticonvulsant, a mood stabilizer, a gamma-aminobutyric acid (GABA) agonist e.g., a GABA-B agonist, a GABA modulator, a stimulant, a β-blocker, a hormone, or a combination thereof 3.23 Any of Methods 3 or 3.1-3.22 wherein (1R,5S)-1-(naphthalen-2-yl)-3-azabicyclo[3.1.0]hexane, in free or pharmaceutically acceptable salt form, is administered concurrently or sequentially, in either order, with fenobam, mavoglurant (AFQ056), dipraglurant, RO4917523, STX107, 2-methyl-6-phenylethynyl pyridine (MPEP), CX516, memantine, acamprosate, minocycline, clonidine, guanfacine, aripiprazole, risperidone, citalopram, escitalopram, fluoxetine, sertraline, fluovoxamine, paroxetine, trazodone, bupropion, imipramine, amitriptyline, venlafaxine, nefazodone, duloxetine, venlafaxine, carbamazepine, lamotrigine, valproic acid, sodium valproate, lithium, quetiapine, folic acid, L-acetylcarnitine, melatonin, arbaclofen, donepezil hydrochloride, alpha-tocopherol, methylphenidate, amphetamine mixed salts (e.g., Adderall), dextroamphetamine, risperidone, olanzapine, ziprasidone, buspirone, filuzole, metadoxine, primidone, topiramate, estradiol, cyclic medroxyprogesterone, or a combination thereof 3.24 Any of Methods 3 or 3.1-3.23 further comprising administering an mGluR5 antagonist.

3.25 Method 3.24 comprising administering fenobam, mavoglurant (AFQ056), dipraglurant, RO4917523, STX107, 2-methyl-6-phenylethynyl pyridine (MPEP), or a combination thereof 3.26 Method 3.25 comprising administering RO4917523, mavoglurant (AFQ056), or a combination thereof 3.27 Any of Methods 3 or 3.1-3.26 further comprising administering a GABA-B agonist.

3.28 Method 3.27 comprising administering arbaclofen.

3.29 Any of Methods 3 or 3.1-3.28 further comprising administering a GABA modulator.

3.30 Method 3.29 comprising administering acamprosate.

3.31 Any of Methods 3 or 3.1-3.30 further comprising administering minocycline.

3.32 Any of Methods 3 or 3.1-3.31 further comprising a non-pharmacological intervention, e.g., a modification in the home environment, a more tailored behavioral intervention and classroom environment, language and occupational therapy, an attention to social factors, sensory integration therapy, or a combination thereof 3.33 Any of Methods 3 or 3.1-3.32 wherein the (1R,5S)-1-(naphthalen-2-yl)-3-azabicyclo[3.1.0]hexane, in free or pharmaceutically acceptable salt form, is administered in a sustained release pharmaceutical composition.

3.34 Method 3.33 wherein the $C_{max}$ of (1R,5S)-1-(naphthalen-2-yl)-3-azabicyclo[3.1.0]hexane, in free or pharmaceutically acceptable salt form, provided after administration of the sustained release pharmaceutical composition is less than about 80%, e.g., less than about 75%, e.g., less than about 60%, e.g., less than about 50%, e.g., less than about 40%, e.g., less than about 30%, e.g., is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

3.35 Method 3.34 wherein the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, e.g., is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

3.36 Any of Methods 3 or 3.1-3.35 wherein the fragile X-associated disorder is fragile X syndrome (FXS).

3.37 Any of Methods 3 or 3.1-3.35 wherein the fragile X-associated disorder is fragile X-associated tremor/ataxia syndrome (FXTAS).

3.38 Any of Methods 3 or 3.1-3.35 wherein the fragile X-associated disorder is fragile X-associated primary ovarian insufficiency (FXPOI).

3.39 Any of Methods 3 or 3.1-3.35 wherein the fragile X-associated disorder is associated with an expansion to 40, e.g., 44 or more, e.g., 50 or more, e.g., 54 or more, e.g., 80 or more, e.g, 100 or more, e.g., 200 or more repeats, of the cytosine guanine guanine (CGG) trinucleotide within the 5' untranslated region of the FMR1 gene located on the X chromosome.

Also provided is use of (1R,5S)-1-(naphthalen-2-yl)-3-azabicyclo[3.1.0]hexane, in free or pharmaceutically acceptable salt form, in the manufacture of a medicament for treating autism spectrum disorder in a patient in need thereof, wherein the patient has a fragile X-associated disorder, e.g., for use in Method 3, e.g., Methods 3.1-3.39.

Also provided is a pharmaceutical composition comprising (1R,5S)-1-(naphthalen-2-yl)-3-azabicyclo[3.1.0]hexane, in free or pharmaceutically acceptable salt form, in combination with a pharmaceutically acceptable diluent or carrier for use in treating autism spectrum disorder in a patient in need thereof, wherein the patient has a fragile X-associated disorder, e.g., for use in Method 3, e.g., Methods 3.1-3.39.

Also provided is a method (Method 4) of treating a patient having a fragile X-associated disorder comprising administering to the patient in need thereof a therapeutically effective amount of (1R,5S)-1-(naphthalen-2-yl)-3-azabicyclo[3.1.0]hexane, in free or pharmaceutically acceptable salt form, wherein the patient was refractory to a prior course of treatment for the fragile X-associated disorder.

Further provided is Method 4 as follows:

4.1 Method 4 wherein the therapeutically effective amount of (1R,5S)-1-(naphthalen-2-yl)-3-azabicyclo[3.1.0]hexane, in free or pharmaceutically acceptable salt form, is substantially free of the corresponding (−) enantiomer.

4.2 Method 4 or 4.1 wherein the therapeutically effective amount of (1R,5S)-1-(naphthalen-2-yl)-3-azabicyclo

[3.1.0]hexane, in free or pharmaceutically acceptable salt form, comprises less than or equal to 20% w/w of the corresponding (−) enantiomer.

4.3 Method 4, 4.1, or 4.2 wherein the therapeutically effective amount of (1R,5S)-1-(naphthalen-2-yl)-3-azabicyclo[3.1.0]hexane, in free or pharmaceutically acceptable salt form, comprises less than or equal to 10% w/w of the corresponding (−) enantiomer.

4.4 Any of Methods 4 or 4.1-4.3 wherein the therapeutically effective amount of (1R,5S)-1-(naphthalen-2-yl)-3-azabicyclo[3.1.0]hexane, in free or pharmaceutically acceptable salt form, comprises less than or equal to 5% w/w of the corresponding (−) enantiomer.

4.5 Any of Methods 4 or 4.1-4.4 wherein the therapeutically effective amount of (1R,5S)-1-(naphthalen-2-yl)-3-azabicyclo[3.1.0]hexane, in free or pharmaceutically acceptable salt form, comprises less than or equal to 2% w/w of the corresponding (−) enantiomer.

4.6 Any of Methods 4 or 4.1-4.5 wherein the therapeutically effective amount of (1R,5S)-1-(naphthalen-2-yl)-3-azabicyclo[3.1.0]hexane, in free or pharmaceutically acceptable salt form, comprises less than or equal to 1% w/w of the corresponding (−) enantiomer.

4.7 Any of Methods 4 or 4.1-4.6 wherein (1R,5S)-1-(naphthalen-2-yl)-3-azabicyclo[3.1.0]hexane is in pharmaceutically acceptable salt form.

4.8 Method 4.7 wherein (1R,5S)-1-(naphthalen-2-yl)-3-azabicyclo[3.1.0]hexane in pharmaceutically acceptable salt form is an acid addition salt.

4.9 Method 4.8 wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo[3.1.0]hexane hydrochloride.

4.10 Any of Methods 4 or 4.1-4.9 wherein (1R,5S)-1-(naphthalen-2-yl)-3-azabicyclo[3.1.0]hexane, in free or pharmaceutically acceptable salt form, is crystalline.

4.11 Any of Methods 4 or 4.1-4.10 comprising administering 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of (1R,5S)-1-(naphthalen-2-yl)-3-azabicyclo[3.1.0]hexane, in free or pharmaceutically acceptable salt form.

4.12 Any of Methods 4 or 4.1-4.11 comprising administering 75 mg to 1000 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

4.13 Any of Methods 4 or 4.1-4.11 comprising administering 50 mg to 600 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

4.14 Any of Methods 4 or 4.1-4.11 comprising administering 5 mg to 500 mg, e.g., 5 mg to 10 mg, e.g, 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of (1R,5S)-1-(naphthalen-2-yl)-3-azabicyclo[3.1.0]hexane, in free or pharmaceutically acceptable salt form.

4.15 Any of Methods 4 or 4.1-4.10 comprising administering 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of (1R,5S)-1-(naphthalen-2-yl)-3-azabicyclo[3.1.0]hexane, in free or pharmaceutically acceptable salt forms.

4.16 Any of Methods 4 or 4.1-4.15 comprising administering (1R,5S)-1-(naphthalen-2-yl)-3-azabicyclo[3.1.0]hexane, in free or pharmaceutically acceptable salt form, once, twice, three, or four times daily.

4.17 Any of Methods 4 or 4.1-4.16 comprising administering (1R,5S)-1-(naphthalen-2-yl)-3-azabicyclo[3.1.0]hexane, in free or pharmaceutically acceptable salt form, once daily.

4.18 Any of Methods 4 or 4.1-4.17 comprising administering (1R,5S)-1-(naphthalen-2-yl)-3-azabicyclo[3.1.0]hexane, in free or pharmaceutically acceptable salt form, twice daily.

4.19 Any of Methods 4 or 4.1-4.18 comprising administering (1R,5S)-1-(naphthalen-2-yl)-3-azabicyclo[3.1.0]hexane, in free or pharmaceutically acceptable salt form, three times daily.

4.20 Any of Methods 4 or 4.1-4.19 comprising administering (1R,5S)-1-(naphthalen-2-yl)-3-azabicyclo[3.1.0]hexane, in free or pharmaceutically acceptable salt form, four times daily.

4.21 Any of Methods 4 or 4.1-4.20 wherein (1R,5S)-1-(naphthalen-2-yl)-3-azabicyclo[3.1.0]hexane, in free or pharmaceutically acceptable salt form, is administered concurrently or sequentially, in either order, with another drug.

4.22 Any of Methods 4 or 4.1-4.21 wherein (1R,5S)-1-(naphthalen-2-yl)-3-azabicyclo[3.1.0]hexane, in free or pharmaceutically acceptable salt form, is administered concurrently or sequentially, in either order, with an mGluR1 antagonist, an mGluR2/3 antagonist, an mGluR5 antagonist, an AMPA receptor positive modulator, an NMDA receptor antagonist, a tetracycline antibiotic, an α2-adrenergic agonist, an antipsychotic, an anti-depressant (e.g., a selective serotonin reuptake inhibitor (SSRI), a serotonin-norepinephrine reuptake inhibitor (SNRI), or a tricyclic anti-depressant), a benzodiazepine, an anticonvulsant, a mood stabilizer, a gamma-aminobutyric acid (GABA) agonist e.g., a GABA-B agonist, a GABA modulator, a stimulant, a β-blocker, a hormone, or a combination thereof 4.23 Any of Methods 4 or 4.1-4.22 wherein (1R,5S)-1-(naphthalen-2-yl)-3-azabicyclo[3.1.0]hexane, in free or pharmaceutically acceptable salt form, is administered concurrently or sequentially, in either order, with fenobam, mavoglurant (AFQ056), dipraglurant, RO4917523, STX107, 2-methyl-6-phenylethynyl pyridine (MPEP), CX516, memantine, acamprosate, minocycline, clonidine, guanfacine, aripiprazole, risperidone, citalopram, escitalopram, fluoxetine, sertraline, fluvoxamine, paroxetine, trazodone, bupropion, imipramine, amitriptyline, venlafaxine, nefazodone, duloxetine, venlafaxine, carbamazepine, lamotrigine, valproic acid, sodium valproate, lithium, quetiapine, folic acid, L-acetylcarnitine, melatonin, arbaclofen, donepezil hydrochloride, alpha-tocopherol, methylphenidate, amphetamine mixed salts (e.g., Adderall), dextroamphetamine, risperidone, olanzapine, ziprasidone, buspirone, filuzole, metadoxine, primidone, topiramate, estradiol, cyclic medroxyprogesterone, or a combination thereof 4.24 Any of Methods 4 or 4.1-4.23 further comprising administering an mGluR5 antagonist.

4.25 Method 4.24 comprising administering fenobam, mavoglurant (AFQ056), dipraglurant, RO4917523, STX107, 2-methyl-6-phenylethynyl pyridine (MPEP), or a combination thereof 4.26 Method 4.25 comprising administering RO4917523, mavoglurant (AFQ056), or a combination thereof 4.27 Any of Methods 4 or 4.1-4.26 further comprising administering a GABA-B agonist.

4.28 Method 4.27 comprising administering arbaclofen.

4.29 Any of Methods 4 or 4.1-4.28 further comprising administering a GABA modulator.

4.30 Method 4.29 comprising administering acamprosate.

4.31 Any of Methods 4 or 4.1-4.30 further comprising administering minocycline.

4.32 Any of Methods 4 or 4.1-4.31 further comprising a non-pharmacological intervention, e.g., a modification in the home environment, a more tailored behavioral intervention and classroom environment, language and occupational therapy, an attention to social factors, sensory integration therapy, or a combination thereof.

4.33 Any of Methods 4 or 4.1-4.32 wherein the (1R,5S)-1-(naphthalen-2-yl)-3-azabicyclo[3.1.0]hexane, in free or pharmaceutically acceptable salt form, is administered in a sustained release pharmaceutical composition.

4.34 Method 4.33 wherein the $C_{max}$ of (1R,5S)-1-(naphthalen-2-yl)-3-azabicyclo[3.1.0]hexane, in free or pharmaceutically acceptable salt form, provided after administration of the sustained release pharmaceutical composition is less than about 80%, e.g., less than about 75%, e.g., less than about 60%, e.g., less than about 50%, e.g., less than about 40%, e.g., less than about 30%, e.g., is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

4.35 Method 4.34 wherein the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, e.g., is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

4.36 Any of Methods 4 or 4.1-4.35 wherein the fragile X-associated disorder is fragile X syndrome (FXS).

4.37 Any of Methods 4 or 4.1-4.35 wherein the fragile X-associated disorder is fragile X-associated tremor/ataxia syndrome (FXTAS).

4.38 Any of Methods 4 or 4.1-4.35 wherein the fragile X-associated disorder is fragile X-associated primary ovarian insufficiency (FXPOI).

4.39 Any of Methods 4 or 4.1-4.35 wherein the fragile X-associated disorder is associated with an expansion to 40, e.g., 44 or more, e.g., 50 or more, e.g., 54 or more, e.g., 80 or more, e.g, 100 or more, e.g., 200 or more repeats, of the cytosine guanine guanine (CGG) trinucleotide within the 5' untranslated region of the FMR1 gene located on the X chromosome.

4.40 Any of Methods 4 or 4.1-4.39, wherein the treatment improves one or more symptoms associated with the fragile X-associated disorder.

4.41 Method 4.41 wherein the one or more symptoms comprise one or more of cognitive impairment, anxiety, hyperactivity, impulsivity, repetitive/perseverative stereotypic behaviors, unstable affect, aggression, and self-injurious behavior.

Also provided is use of (1R,5S)-1-(naphthalen-2-yl)-3-azabicyclo[3.1.0]hexane, in free or pharmaceutically acceptable salt form, in the manufacture of a medicament for treating a patient having a fragile X-associated disorder, wherein the patient was refractory to a prior course of treatment for the fragile X-associated disorder, e.g., for use in Method 4, e.g., Methods 4.1-4.41.

Also provided is a pharmaceutical composition comprising (1R,5S)-1-(naphthalen-2-yl)-3-azabicyclo[3.1.0]hexane, in free or pharmaceutically acceptable salt form, in combination with a pharmaceutically acceptable diluent or carrier for use in treating a patient having a fragile X-associated disorder, wherein the patient was refractory to a prior course of treatment for the fragile X-associated disorder, e.g., for use in Method 4, e.g., Methods 4.1-4.41.

Also provided is a method (Method 5) of treating attention-deficit/hyperactivity disorder (ADHD) comprising administering a therapeutically effective amount of (1R,5S)-1-(naphthalen-2-yl)-3-azabicyclo[3.1.0]hexane, in free or pharmaceutically acceptable salt form, to a patient in need thereof wherein the ADHD is co-morbid with one or both of anxiety and depression (e.g., depression), e.g., in a patient with a fragile X-associated disorder.

Further provided is Method 5 as follows:

5.1 Method 5 wherein the therapeutically effective amount of (1R,5S)-1-(naphthalen-2-yl)-3-azabicyclo[3.1.0]hexane, in free or pharmaceutically acceptable salt form, is substantially free of the corresponding (−) enantiomer.

5.2 Method 5 or 5.1 wherein the therapeutically effective amount of (1R,5S)-1-(naphthalen-2-yl)-3-azabicyclo[3.1.0]hexane, in free or pharmaceutically acceptable salt form, comprises less than or equal to 20% w/w of the corresponding (−) enantiomer.

5.3 Method 5, 5.1 or 5.2 wherein the therapeutically effective amount of (1R,5S)-1-(naphthalen-2-yl)-3-azabicyclo[3.1.0]hexane, in free or pharmaceutically acceptable salt form, comprises less than or equal to 10% w/w of the corresponding (−) enantiomer.

5.4 Any of Methods 5 or 5.1-5.3 wherein the therapeutically effective amount of (1R,5S)-1-(naphthalen-2-yl)-3-azabicyclo[3.1.0]hexane, in free or pharmaceutically acceptable salt form, comprises less than or equal to 5% w/w of the corresponding (−) enantiomer.

5.5 Any of Methods 5 or 5.1-5.4 wherein the therapeutically effective amount of (1R,5S)-1-(naphthalen-2-yl)-3-azabicyclo[3.1.0]hexane, in free or pharmaceutically acceptable salt form, comprises less than or equal to 2% w/w of the corresponding (−) enantiomer.

5.6 Any of Methods 5 or 5.1-5.5 wherein the therapeutically effective amount of (1R,5S)-1-(naphthalen-2-yl)-3-azabicyclo[3.1.0]hexane, in free or pharmaceutically acceptable salt form, comprises less than or equal to 1% w/w of the corresponding (−) enantiomer.

5.7 Any of Methods 5 or 5.1-5.6 wherein (1R,5S)-1-(naphthalen-2-yl)-3-azabicyclo[3.1.0]hexane is in pharmaceutically acceptable salt form.

5.8 Method 5.7 wherein (1R,5S)-1-(naphthalen-2-yl)-3-azabicyclo[3.1.0]hexane in pharmaceutically acceptable salt form is an acid addition salt.

5.9 Method 5.8 wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo[3.1.0]hexane hydrochloride.

5.10 Any of Methods 5 or 5.1-5.9 wherein (1R,5S)-1-(naphthalen-2-yl)-3-azabicyclo[3.1.0]hexane, in free or pharmaceutically acceptable salt form, is crystalline.

5.11 Any of Methods 5 or 5.1-5.10 comprising administering 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of (1R,5S)-1-(naphthalen-2-yl)-3-azabicyclo[3.1.0]hexane, in free or pharmaceutically acceptable salt form.

5.12 Any of Methods 5 or 5.1-5.11 comprising administering 75 mg to 1000 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

5.13 Any of Methods 5 or 5.1-5.11 comprising administering 50 mg to 600 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

5.14 Any of Methods 5 or 5.1-5.11 comprising administering 5 mg to 500 mg, e.g., 5 mg to 10 mg, e,g, 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of (1R,5S)-1-(naphthalen-2-yl)-3-azabicyclo[3.1.0]hexane, in free or pharmaceutically acceptable salt form.

5.15 Any of Methods 5 or 5.1-5.10 comprising administering 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of (1R,5S)-1-(naphthalen-2-yl)-3-azabicyclo[3.1.0]hexane, in free or pharmaceutically acceptable salt form.

5.16 Any of Methods 5 or 5.1-5.15 comprising administering (1R,5S)-1-(naphthalen-2-yl)-3-azabicyclo[3.1.0]hexane, in free or pharmaceutically acceptable salt form, once, twice, three, or four times daily.

5.17 Any of Methods 5 or 5.1-5.16 comprising administering (1R,5S)-1-(naphthalen-2-yl)-3-azabicyclo[3.1.0]hexane, in free or pharmaceutically acceptable salt form, once daily.

5.18 Any of Methods 5 or 5.1-5.17 comprising administering (1R,5S)-1-(naphthalen-2-yl)-3-azabicyclo[3.1.0]hexane, in free or pharmaceutically acceptable salt form, twice daily.

5.19 Any of Methods 5 or 5.1-5.18 comprising administering (1R,5S)-1-(naphthalen-2-yl)-3-azabicyclo[3.1.0]hexane, in free or pharmaceutically acceptable salt form, three times daily.

5.20 Any of Methods 5 or 5.1-5.19 comprising administering (1R,5S)-1-(naphthalen-2-yl)-3-azabicyclo[3.1.0]hexane, in free or pharmaceutically acceptable salt form, four times daily.

5.21 Any of Methods 5 or 5.1-5.20 wherein (1R,5S)-1-(naphthalen-2-yl)-3-azabicyclo[3.1.0]hexane, in free or pharmaceutically acceptable salt form, is administered concurrently or sequentially, in either order, with another drug.

5.22 Any of Methods 5 or 5.1-5.21 wherein (1R,5S)-1-(naphthalen-2-yl)-3-azabicyclo[3.1.0]hexane, in free or pharmaceutically acceptable salt form, is administered concurrently or sequentially, in either order, with an mGluR1 antagonist, an mGluR2/3 antagonist, an mGluR5 antagonist, an AMPA receptor positive modulator, an NMDA receptor antagonist, a tetracycline antibiotic, an α2-adrenergic agonist, an antipsychotic, an anti-depressant (e.g., a selective serotonin reuptake inhibitor (SSRI), a serotonin-norepinephrine reuptake inhibitor (SNRI), or a tricyclic anti-depressant), a benzodiazepine, an anti-convulsant, a mood stabilizer, a gamma-aminobutyric acid (GABA) agonist e.g., a GABA-B agonist, a GABA modulator, a stimulant, a β-blocker, a hormone, or a combination thereof 5.23 Any of Methods 5 or 5.1-5.22 wherein (1R,5S)-1-(naphthalen-2-yl)-3-azabicyclo[3.1.0]hexane, in free or pharmaceutically acceptable salt form, is administered concurrently or sequentially, in either order, with fenobam, mavoglurant (AFQ056), dipraglurant, RO4917523, STX107, 2-methyl-6-phenylethynyl pyridine (MPEP), CX516, memantine, acamprosate, minocycline, clonidine, guanfacine, aripiprazole, risperidone, citalopram, escitalopram, fluoxetine, sertraline, fluovoxamine, paroxetine, trazodone, bupropion, imipramine, amitriptyline, venlafaxine, nefazodone, duloxetine, venlafaxine, carbamazepine, lamotrigine, valproic acid, sodium valproate, lithium, quetiapine, folic acid, L-acetylcarnitine, melatonin, arbaclofen, donepezil hydrochloride, alpha-tocopherol, methylphenidate, amphetamine mixed salts (e.g., Adderall), dextroamphetamine, risperidone, olanzapine, ziprasidone, buspirone, filuzole, metadoxine, primidone, topiramate, estradiol, cyclic medroxyprogesterone, or a combination thereof 5.24 Any of Methods 5 or 5.1-5.23 further comprising administering an mGluR5 antagonist.

5.25 Method 5.24 comprising administering fenobam, mavoglurant (AFQ056), dipraglurant, RO4917523, STX107, 2-methyl-6-phenylethynyl pyridine (MPEP), or a combination thereof 5.26 Method 5.25 comprising administering RO4917523, mavoglurant (AFQ056), or a combination thereof 5.27 Any of Methods 5 or 5.1-5.26 further comprising administering a GABA-B agonist.

5.28 Method 5.27 comprising administering arbaclofen.

5.29 Any of Methods 5 or 5.1-5.28 further comprising administering a GABA modulator.

5.30 Method 5.29 comprising administering acamprosate.

5.31 Any of Methods 5 or 5.1-5.30 further comprising administering minocycline.

5.32 Any of Methods 5 or 5.1-5.31 further comprising a non-pharmacological intervention, e.g., a modification in the home environment, a more tailored behavioral intervention and classroom environment, language and occupational therapy, an attention to social factors, sensory integration therapy, or a combination thereof 5.33 Any of Methods 5 or 5.1-5.32 wherein the (1R,5S)-1-(naphthalen-2-yl)-3-azabicyclo[3.1.0]hexane, in free or pharmaceutically acceptable salt form, is administered in a sustained release pharmaceutical composition.

5.34 Method 5.33 wherein the $C_{max}$ of (1R,5S)-1-(naphthalen-2-yl)-3-azabicyclo[3.1.0]hexane, in free or pharmaceutically acceptable salt form, provided after administration of the sustained release pharmaceutical composition is less than about 80%, e.g., less than about 75%, e.g., less than about 60%, e.g., less than about 50%, e.g., less than about 40%, e.g., less than about 30%, e.g., is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R, 5S)-1-(naphthalen-2-yl)-3-azabicyclo[3.1.0]hexane, in free or pharmaceutically acceptable salt form, in an immediate release pharmaceutical composition.

5.35 Method 5.34 wherein the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, e.g., is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

5.36 Any of Methods 5 or 5.1-5.35 wherein the patient has a fragile X-associated disorder, e.g., fragile X syndrome (FXS).

5.37 Any of Methods 5 or 5.1-5.35 wherein the patient has a fragile X-associated disorder, e.g., fragile X-associated tremor/ataxia syndrome (FXTAS).

5.38 Any of Methods 5 or 5.1-5.35 wherein the patient has a fragile X-associated disorder, e.g., fragile X-associated primary ovarian insufficiency (FXPOI).

5.39 Any of Methods 5 or 5.1-5.35 wherein the patient has a fragile X-associated disorder, e.g., a fragile X-associated disorder associated with an expansion to 40, e.g., 50 or more, e.g., 54 or more, e.g., 80 or more, e.g, 100 or more, e.g., 200 or more repeats, of the cytosine guanine guanine (CGG) trinucleotide within the 5' untranslated region of the FMR1 gene located on the X chromosome.

5.40 Any of Methods 5 or 5.1-5.39 wherein the ADHD is predominantly inattentive type.

5.41 Any of Methods 5 or 5.1-5.39 wherein the ADHD is predominantly hyperactive-impulsive type.

5.42 Any of Methods 5 or 5.1-5.39 wherein the ADHD is combined type.

Also provided is use of (1R,5S)-1-(naphthalen-2-yl)-3-azabicyclo[3.1.0]hexane, in free or pharmaceutically acceptable salt form, in the manufacture of a medicament for treating attention-deficit/hyperactivity disorder (ADHD) wherein the ADHD is co-morbid with one or both of anxiety and depression (e.g., depression), e.g., in a patient with a fragile X-associated disorder, e.g., for use in Method 5, e.g., Methods 5.1-5.42.

Also provided is a pharmaceutical composition comprising (1R,5S)-1-(naphthalen-2-yl)-3-azabicyclo[3.1.0]hexane, in free or pharmaceutically acceptable salt form in combination with a pharmaceutically acceptable diluent or carrier for use in treating attention-deficit/hyperactivity disorder (ADHD) wherein the ADHD is co-morbid with one or both of anxiety and depression (e.g., depression), e.g., in a patient with a fragile X-associated disorder, e.g., for use in Method 5, e.g., Methods 5.1-5.42.

Also provided is a method (Method 6) of treating an autism spectrum disorder comprising administering a therapeutically effective amount of (1R,5S)-1-(naphthalen-2-yl)-3-azabicyclo[3.1.0]hexane, in free or pharmaceutically acceptable salt form, to a patient in need thereof wherein the autism spectrum disorder is co-morbid with one or both of anxiety and depression (e.g., depression), e.g., in a patient with a fragile X-associated disorder.

Further provided is Method 6 as follows:

6.1 Method 6 wherein the therapeutically effective amount of (1R,5S)-1-(naphthalen-2-yl)-3-azabicyclo[3.1.0]hexane, in free or pharmaceutically acceptable salt form, is substantially free of the corresponding (−) enantiomer.

6.2 Method 6 or 6.1 wherein the therapeutically effective amount of (1R,5S)-1-(naphthalen-2-yl)-3-azabicyclo[3.1.0]hexane, in free or pharmaceutically acceptable salt form, comprises less than or equal to 20% w/w of the corresponding (−) enantiomer.

6.3 Method 6, 6.1 or 6.2 wherein the therapeutically effective amount of (1R,5S)-1-(naphthalen-2-yl)-3-azabicyclo[3.1.0]hexane, in free or pharmaceutically acceptable salt form, comprises less than or equal to 10% w/w of the corresponding (−) enantiomer.

6.4 Any of Methods 6 or 6.1-6.3 wherein the therapeutically effective amount of (1R,5S)-1-(naphthalen-2-yl)-3-azabicyclo[3.1.0]hexane, in free or pharmaceutically acceptable salt form, comprises less than or equal to 5% w/w of the corresponding (−) enantiomer.

6.5 Any of Methods 6 or 6.1-6.4 wherein the therapeutically effective amount of (1R,5S)-1-(naphthalen-2-yl)-3-azabicyclo[3.1.0]hexane, in free or pharmaceutically acceptable salt form, comprises less than or equal to 2% w/w of the corresponding (−) enantiomer.

6.6 Any of Methods 6 or 6.1-6.5 wherein the therapeutically effective amount of (1R,5S)-1-(naphthalen-2-yl)-3-azabicyclo[3.1.0]hexane, in free or pharmaceutically acceptable salt form, comprises less than or equal to 1% w/w of the corresponding (−) enantiomer.

6.7 Any of Methods 6 or 6.1-6.6 wherein (1R,5S)-1-(naphthalen-2-yl)-3-azabicyclo[3.1.0]hexane is in pharmaceutically acceptable salt form.

6.8 Method 6.7 wherein (1R,5S)-1-(naphthalen-2-yl)-3-azabicyclo[3.1.0]hexane in pharmaceutically acceptable salt form is an acid addition salt.

6.9 Method 6.8 wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo[3.1.0]hexane hydrochloride.

6.10 Any of Methods 6 or 6.1-6.9 wherein (1R,5S)-1-(naphthalen-2-yl)-3-azabicyclo[3.1.0]hexane, in free or pharmaceutically acceptable salt form, is crystalline.

6.11 Any of Methods 6 or 6.1-6.10 comprising administering 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of (1R,5S)-1-(naphthalen-2-yl)-3-azabicyclo[3.1.0]hexane, in free or pharmaceutically acceptable salt form.

6.12 Any of Methods 6 or 6.1-6.11 comprising administering 75 mg to 1000 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

6.13 Any of Methods 6 or 6.1-6.11 comprising administering 50 mg to 600 mg, e.g., 100 mg to 600 mg, e.g., 100 mg to 400 mg, e.g., 100 mg to 200 mg, of (1R,5S)-1-(naphthalen-2-yl)-3-azabicyclo[3.1.0]hexane, in free or pharmaceutically acceptable salt form.

6.14 Any of Methods 6 or 6.1-6.11 comprising administering 5 mg to 500 mg, e.g., 5 mg to 10 mg, e.g, 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of (1R,5S)-1-(naphthalen-2-yl)-3-azabicyclo[3.1.0]hexane, in free or pharmaceutically acceptable salt form.

6.15 Any of Methods 6 or 6.1-6.10 comprising administering 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of (1R,5S)-1-(naphthalen-2-yl)-3-azabicyclo[3.1.0]hexane, in free or pharmaceutically acceptable salt form.

6.16 Any of Methods 6 or 6.1-6.15 comprising administering (1R,5S)-1-(naphthalen-2-yl)-3-azabicyclo[3.1.0]hexane, in free or pharmaceutically acceptable salt form, once, twice, three, or four times daily.

6.17 Any of Methods 6 or 6.1-6.16 comprising administering (1R,5S)-1-(naphthalen-2-yl)-3-azabicyclo[3.1.0]hexane, in free or pharmaceutically acceptable salt form, once daily.

6.18 Any of Methods 6 or 6.1-6.17 comprising administering (1R,5S)-1-(naphthalen-2-yl)-3-azabicyclo[3.1.0]hexane, in free or pharmaceutically acceptable salt form, twice daily.

6.19 Any of Methods 6 or 6.1-6.18 comprising administering (1R,5S)-1-(naphthalen-2-yl)-3-azabicyclo[3.1.0]hexane, in free or pharmaceutically acceptable salt form, three times daily.

6.20 Any of Methods 6 or 6.1-6.19 comprising administering (1R,5S)-1-(naphthalen-2-yl)-3-azabicyclo[3.1.0]hexane, in free or pharmaceutically acceptable salt form, four times daily.

6.21 Any of Methods 6 or 6.1-6.20 wherein (1R,5S)-1-(naphthalen-2-yl)-3-azabicyclo[3.1.0]hexane, in free or pharmaceutically acceptable salt form, is administered concurrently or sequentially, in either order, with another drug.

6.22 Any of Methods 6 or 6.1-6.21 wherein (1R,5S)-1-(naphthalen-2-yl)-3-azabicyclo[3.1.0]hexane, in free or pharmaceutically acceptable salt form, is administered concurrently or sequentially, in either order, with an mGluR1 antagonist, an mGluR2/3 antagonist, an mGluR5 antagonist, an AMPA receptor positive modulator, an NMDA receptor antagonist, a tetracycline antibiotic, an α2-adrenergic agonist, an antipsychotic, an anti-depressant (e.g., a selective serotonin reuptake inhibitor (SSRI), a serotonin-norepinephrine reuptake inhibitor (SNRI), or a tricyclic anti-depressant), a benzodiazepine, an anti-convulsant, a mood stabilizer, a gamma-aminobutyric acid (GABA) agonist e.g., a GABA-B agonist, a GABA modulator, a stimulant, a β-blocker, a hormone, or a combination thereof 6.23 Any of Methods 6 or 6.1-6.22 wherein (1R,5S)-1-(naphthalen-2-yl)-3-azabicyclo[3.1.0]hexane, in free or pharmaceutically acceptable salt form, is administered concurrently or sequentially, in either order, with fenobam, mavoglurant (AFQ056), dipraglurant, RO4917523, STX107, 2-methyl-6-phenylethynyl pyridine (MPEP), CX516, memantine, acamprosate, minocycline, clonidine, guanfacine, aripiprazole, risperidone, citalopram, escitalopram, fluoxetine, sertraline, fluovoxamine, paroxetine, trazodone, bupropion, imipramine, amitriptyline, venlafaxine, nefazodone, duloxetine, venlafaxine, carbamazepine, lamotrigine, valproic acid, sodium valproate, lithium, quetiapine, folic acid, L-acetylcarnitine, melatonin, arbaclofen, donepezil hydrochloride, alpha-tocopherol, methylphenidate, amphetamine mixed salts (e.g., Adderall), dextroamphetamine, risperidone, olanzapine, ziprasidone, buspirone, filuzole, metadoxine, primidone, topiramate, estradiol, cyclic medroxyprogesterone, or a combination thereof 6.24 Any of Methods 6 or 6.1-6.23 further comprising administering an mGluR5 antagonist.

6.25 Method 6.24 comprising administering fenobam, mavoglurant (AFQ056), dipraglurant, RO4917523, STX107, 2-methyl-6-phenylethynyl pyridine (MPEP), or a combination thereof 6.26 Method 6.25 comprising administering RO4917523, mavoglurant (AFQ056), or a combination thereof 6.27 Any of Methods 6 or 6.1-6.26 further comprising administering a GABA-B agonist.

6.28 Method 6.27 comprising administering arbaclofen.

6.29 Any of Methods 6 or 6.1-6.28 further comprising administering a GABA modulator.

6.30 Method 6.29 comprising administering acamprosate.

6.31 Any of Methods 6 or 6.1-6.30 further comprising administering minocycline.

6.32 Any of Methods 6 or 6.1-6.31 further comprising a non-pharmacological intervention, e.g., a modification in the home environment, a more tailored behavioral intervention and classroom environment, language and occupational therapy, an attention to social factors, sensory integration therapy, or a combination thereof 6.33 Any of Methods 6 or 6.1-6.32 wherein the (1R,5S)-1-(naphthalen-2-yl)-3-azabicyclo[3.1.0]hexane, in free or pharmaceutically acceptable salt form, is administered in a sustained release pharmaceutical composition.

6.34 Method 6.33 wherein the $C_{max}$ of (1R,5S)-1-(naphthalen-2-yl)-3-azabicyclo[3.1.0]hexane, in free or pharmaceutically acceptable salt form, provided after administration of the sustained release pharmaceutical composition is less than about 80%, e.g., less than about 75%, e.g., less than about 60%, e.g., less than about 50%, e.g., less than about 40%, e.g., less than about 30%, e.g., is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

6.35 Method 6.34 wherein the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, e.g., is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

6.36 Any of Methods 6 or 6.1-6.35 wherein the patient has a fragile X-associated disorder, e.g., fragile X syndrome (FXS).

6.37 Any of Methods 6 or 6.1-6.35 wherein the patient has a fragile X-associated disorder, e.g., fragile X-associated tremor/ataxia syndrome (FXTAS).

6.38 Any of Methods 6 or 6.1-6.35 wherein the patient has a fragile X-associated disorder, e.g., fragile X-associated primary ovarian insufficiency (FXPOI).

6.39 Any of Methods 6 or 6.1-6.35 wherein the patient has a fragile X-associated disorder, e.g., a fragile X-associated disorder associated with an expansion to 40, e.g., 50 or more, e.g., 54 or more, e.g., 80 or more, e.g, 100 or more, e.g., 200 or more repeats, of the cytosine guanine guanine (CGG) trinucleotide within the 5' untranslated region of the FMR1 gene located on the X chromosome.

6.40 Any of Methods 6 or 6.1-6.39 wherein the patient has autistic disorder.

6.41 Any of Methods 6 or 6.1-6.39 wherein the patient has Asperger's disorder (Asperger syndrome).

6.42 Any of Methods 6 or 6.1-6.39 wherein the patient has pervasive developmental disorder not otherwise specified (PDD-NOS).

6.43 Any of Methods 6 or 6.1-6.39 wherein the patient has Rett's disorder (Rett syndrome).

6.44 Any of Methods 6 or 6.1-6.39 wherein the patient has childhood disintegrative disorder (CDD).

Also provided is use of (1R,5S)-1-(naphthalen-2-yl)-3-azabicyclo[3.1.0]hexane, in free or pharmaceutically acceptable salt form, in the manufacture of a medicament for treating an autism spectrum disorder wherein the autism spectrum disorder is co-morbid with one or both of anxiety and depression (e.g., depression), e.g., in a patient with a fragile X-associated disorder, e.g., for use in Method 6, e.g., Methods 6.1-6.44.

Also provided is a pharmaceutical composition comprising (1R,5S)-1-(naphthalen-2-yl)-3-azabicyclo[3.1.0]hexane, in free or pharmaceutically acceptable salt form in combination with a pharmaceutically acceptable diluent or carrier for use in treating an autism spectrum disorder wherein the autism spectrum disorder is co-morbid with one or both of anxiety and depression (e.g., depression), e.g., in a patient with a fragile X-associated disorder, e.g., for use in Method 6, e.g., Methods 6.1-6.44.

Any of the preceding methods, e.g., Method 1, e.g., Methods 1.1-1.41, or, e.g., Method 2, e.g., Methods 2.1-2.39, or, e.g., Method 3, e.g., Method 3.1-3.39, or, e.g., Method 4, e.g., Methods 4.1-4.41, or, e.g., Method 5, e.g., Method 5.1-5.42, or, e.g., Method 6, e.g., 6.1-6.44, or any of the preceding uses or pharmaceutical compositions wherein the therapeutically effective amount of (1R,5S)-1-(naphthalen-2-yl)-3-azabicyclo[3.1.0]hexane, in free or pharmaceutically acceptable salt form, is different, e.g., lower, than the therapeutically effective amount of (1R,5S)-1-(naphthalen-2-yl)-3-azabicyclo[3.1.0]hexane, in free or pharmaceutically acceptable salt form, administered to a patient without a fragile X-associated disorder, e.g., fragile X syndrome. In some embodiments, provided is Method 2, e.g., Methods 2.1-2.39, wherein the therapeutically effective amount of (1R,5S)-1-(naphthalen-2-yl)-3-azabicyclo[3.1.0]hexane, in free or pharmaceutically acceptable salt form, to treat attention-deficit/hyperactivity disorder (ADHD) in a patient with a fragile X-associated disorder, e.g., fragile X syndrome (FXS), is different, e.g., lower, than the therapeutically effective amount of (1R,5S)-1-(naphthalen-2-yl)-3-azabicyclo[3.1.0]hexane, in free or pharmaceutically acceptable salt form, administered to treat attention-deficit/hyperactivity disorder (ADHD) in a patient without a fragile X-associated disorder, e.g., fragile X syndrome.

Any of the preceding methods, e.g., Method 1, e.g., Methods 1.1-1.41, or, e.g., Method 2, e.g., Methods 2.1-2.39, or, e.g., Method 3, e.g., Method 3.1-3.39, or, e.g., Method 4, e.g., Methods 4.1-4.41, or, e.g., Method 5, e.g., Method 5.1-5.42, or, e.g., Method 6, e.g., Method 6.1-6.44, or any of the preceding uses or pharmaceutical compositions wherein the patient exhibits one or more of hyperactivity, impulsivity, inattention, impaired working memory, irritability, depression, dysthymia, impaired executive function (e.g., reasoning, planning, problem solving), mood lability, anxiety, repetitive/perseverative stereotypic behaviors, unstable affect, aggression, and self-injurious behavior.

A dose or method of administration of the dose of the present disclosure is not particularly limited. Dosages employed in practicing the present disclosure will of course vary depending, e.g. on the mode of administration and the therapy desired. In general, satisfactory results, e.g. for the treatment of a fragile X-associated disorder, e.g., fragile X syndrome, are indicated to be obtained on oral administration at dosages of the order from about 0.01 to 2.0 mg/kg. An indicated daily dosage for oral administration may be in the range of from about 0.75 mg to 200 mg, conveniently administered once, or in divided doses 2 to 4 times, daily or in sustained release form. Unit dosage forms for oral administration thus for example may comprise from about 0.2 mg to 75 mg or 150 mg, e.g. from about 0.2 mg or 2.0 mg or 50 mg or 75 mg or 100 mg to 200 mg or 500 mg of (1R,5S)-1-(naphthalen-2-yl)-3-azabicyclo[3.1.0]hexane, in free or pharmaceutically acceptable salt form, together with a pharmaceutically acceptable diluent or carrier therefor.

(1R,5S)-1-(naphthalen-2-yl)-3-azabicyclo[3.1.0]hexane, in free or pharmaceutically acceptable salt form, may be administered by any suitable route, including orally, parenterally, transdermally, or by inhalation, including by sustained release, although various other known delivery routes, devices and methods can likewise be employed. In some embodiments, provided is a sustained release pharmaceutical composition, e.g., an oral sustained release pharmaceutical composition, comprising (1R,5S)-1-(naphthalen-2-yl)-3-azabicyclo[3.1.0]hexane, in free or pharmaceutically acceptable salt form, which provides therapeutically effective levels of (1R,5S)-1-(naphthalen-2-yl)-3-azabicyclo[3.1.0]hexane over a sustained delivery period of approximately 6 hours or longer, e.g., 8 hours or longer, e.g., 12 hours or longer, e.g., 18 hours or longer, e.g., 24 hours or longer. In some embodiments, provided is an immediate release pharmaceutical composition, e.g., an oral immediate release pharmaceutical composition, comprising (1R,5S)-1-(naphthalen-2-yl)-3-azabicyclo[3.1.0]hexane, in free or pharmaceutically acceptable salt form.

In some embodiments, (1R,5S)-1-(naphthalen-2-yl)-3-azabicyclo[3.1.0]hexane, in free or pharmaceutically acceptable salt form, is released from a composition and delivered into the blood plasma or other target site of activity in the subject (including, but not limited to, areas of the brain such as the prefrontal cortex, frontal cortex, thalamus, striatum, ventral tegmental area, other cortical areas, hippocampus, hypothalamus, or nucleus accumbens) in a sustained release profile characterized in that from about 0% to 20% of the active compound is released and delivered (as determined, e.g., by measuring blood plasma levels) within 0 to 2 hours, from 20% to 50% of the active compound is released and delivered within about 2 to 12 hours, from 50% to 85% of the active compound is released and delivered within about 3 to 20 hours, and greater than 75% of the active compound is released and delivered within about 5 to 18 hours.

In some embodiments, the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 80%, e.g., less than about 75%, e.g., less than about 60%, e.g., less than about 50%, e.g., less than about 40%, e.g., less than about 30% of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition. In some embodiments, the $C_{max}$ of (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is about 20-80%, e.g., is about 30-80%, e.g., is about 20-70% e.g., is about 30-70%, e.g., is about 30-60%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition. In some embodiments, the $C_{max}$ (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is less than about 50%, e.g., less than about 40%, e.g., less than about 30%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition. In some embodiments, the $C_{max}$ (1R,5S)-1-(naphthalen-2-yl)-3-azabicyclo[3.1.0]hexane, in free or pharmaceutically acceptable salt form, provided after administration of a sustained release pharmaceutical composition comprising (1R,5S)-1-(naphthalen-2-yl)-3-azabicyclo[3.1.0]hexane, in free or pharmaceutically acceptable salt form, is about 20-50%, e.g., is about 30-50%, e.g., is about 30-40%, of the $C_{max}$ obtained after administering an equivalent dose of (1R,5S)-1-(naphthalen-2-yl)-3-azabicyclo[3.1.0]hexane, in free or pharmaceutically acceptable salt form, in an immediate release pharmaceutical composition.

In some embodiments, the pharmaceutical composition comprising (1R,5S)-1-(naphthalen-2-yl)-3-azabicyclo[3.1.0]hexane, in free or pharmaceutically acceptable salt form, e.g., a sustained release pharmaceutical composition, comprises a lubricant, e.g., magnesium stearate, a carrier, e.g., lactose monohydrate, or a combination thereof.

Pharmaceutical compositions comprising (1R,5S)-1-(naphthalen-2-yl)-3-azabicyclo[3.1.0]hexane, in free or pharmaceutically acceptable salt form, may be prepared using conventional diluents or excipients and techniques known in the galenic art. Thus, oral dosage forms may include tablets, capsules, solutions, suspensions, and the like.

Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective. Indeed, an advantage of administering different agents with different mechanisms of action and different side effect profiles may be to reduce the dosage and side effects of either or both agents, as well as to enhance or potentiate their activity as monotherapy.

EXAMPLE

Example 1

Sustained release pharmaceutical composition comprising (1R,5S)-1-(naphthalen-2-yl)-3-azabicyclo[3.1.0]hexane hydrochloride

| Ingredient | Concentration (% W/W) | Tablet Unit Weight (mg) |
|---|---|---|
| (1R,5S)-1-(naphthalen-2-yl)-3-azabicyclo[3.1.0]hexane hydrochloride | 25% | 100 |
| Lactose, Monohydrate, NF | 74.5% | 298 |
| Hypromellose, NF (as 50/50 premix - RetaLac ®) | | |
| Magnesium Stearate, NF (Hyqual ® Vegetable source) | 0.5% | 2 |
| Total | 100% | 400 |

What is claimed is:

1. A method of treating a fragile X-associated disorder in a human in need thereof comprising administering to the human a therapeutically effective amount of (1R,5S)-1-(naphthalen-2-yl)-3-azabicyclo[3.1.0]hexane, in free or pharmaceutically acceptable salt form, wherein the fragile-X associated disorder is associated with an expansion to 50 or more repeats of the cytosine guanine guanine (CGG) trinucleotide within the 5' untranslated region of the FMR1 gene located on the X chromosome and wherein the fragile X-associated disorder is fragile X syndrome (FXS), fragile X-associated tremor/ataxia syndrome (FXTAS), or fragile X-associated primary ovarian insufficiency (FXPOI).

2. A method of treating attention-deficit/hyperactivity disorder (ADHD) in a human in need thereof comprising administering to the human a therapeutically effective amount of (1R,5S)-1-(naphthalen-2-yl)-3-azabicyclo[3.1.0] hexane, in free or pharmaceutically acceptable salt form, wherein the human has a fragile X-associated disorder associated with an expansion to 50 or more repeats of the cytosine guanine guanine (CGG) trinucleotide within the 5' untranslated region of the FMR1 gene located on the X chromosome.

3. A method of treating autism spectrum disorder (ASD) in a human in need thereof comprising administering to the human a therapeutically effective amount of (1R,5S)-1-(naphthalen-2-yl)-3-azabicyclo[3.1.0]hexane, in free or pharmaceutically acceptable salt form, wherein the human has a fragile X-associated disorder associated with an expansion to 50 or more repeats of the cytosine guanine guanine (CGG) trinucleotide within the 5' untranslated region of the FMR1 gene located on the X chromosome.

4. The method of claim 1, wherein (1R,5S)-1-(naphthalen-2-yl)-3-azabicyclo[3.1.0]hexane is in pharmaceutically acceptable salt form.

5. The method of claim 4, wherein (1R,5S)-1-(naphthalen-2-yl)-3-azabicyclo[3.1.0]hexane in pharmaceutically acceptable salt form is an acid addition salt.

6. The method of claim 5, wherein (1R,5S)-1-(naphthalen-2-yl)-3-azabicyclo[3.1.0]hexane in pharmaceutically acceptable salt form is (1R,5S)-1-(naphthalen-2-yl)-3-azabicyclo[3.1.0]hexane hydrochloride.

7. The method of claim 1 comprising administering 50 mg to 600 mg of (1R,5S)-1-(naphthalen-2-yl)-3-azabicyclo[3.1.0]hexane, in free or pharmaceutically acceptable salt form.

8. The method of claim 1, wherein (1R,5S)-1-(naphthalen-2-yl)-3-azabicyclo[3.1.0]hexane, in free or pharmaceutically acceptable salt form, is administered concurrently or sequentially, in either order, with another drug.

9. The method of claim 1, wherein (1R,5S)-1-(naphthalen-2-yl)-3-azabicyclo[3.1.0]hexane, in free or pharmaceutically acceptable salt form, is administered in a sustained release pharmaceutical composition.

10. The method of claim 1, wherein the fragile X-associated disorder is fragile X syndrome (FXS).

11. The method of claim 1, wherein the fragile X-associated disorder is fragile X-associated tremor/ataxia syndrome (FXTAS).

12. The method of claim 1, wherein the fragile X-associated disorder is fragile X-associated primary ovarian insufficiency (FXPOI).

13. The method of claim 1, wherein the fragile-X associated disorder is associated with an expansion to 54 or more repeats of the cytosine guanine guanine (CGG) trinucleotide within the 5' untranslated region of the FMR1 gene located on the X chromosome.

14. The method of claim 1, wherein the fragile-X associated disorder is associated with an expansion to 80 or more repeats of the cytosine guanine guanine (CGG) trinucleotide within the 5' untranslated region of the FMR1 gene located on the X chromosome.

15. The method of claim 2 comprising administering 50 mg to 600 mg of (1R,5S)-1-(naphthalen-2-yl)-3-azabicyclo[3.1.0]hexane, in free or pharmaceutically acceptable salt form.

16. The method of claim 3 comprising administering 50 mg to 600 mg of (1R,5S)-1-(naphthalen-2-yl)-3-azabicyclo[3.1.0]hexane, in free or pharmaceutically acceptable salt form.

17. The method of claim 2, wherein the fragile X-associated disorder is fragile X syndrome (FXS).

18. The method of claim 2, wherein the fragile X-associated disorder is fragile X-associated tremor/ataxia syndrome (FXTAS).

19. The method of claim 3, wherein the fragile X-associated disorder is fragile X syndrome (FXS).

20. The method of claim 3, wherein the fragile X-associated disorder is fragile X-associated tremor/ataxia syndrome (FXTAS).

* * * * *

UNITED STATES PATENT AND TRADEMARK OFFICE
CERTIFICATE OF CORRECTION

PATENT NO.         : 9,839,627 B2
APPLICATION NO.    : 15/102871
DATED              : December 12, 2017
INVENTOR(S)        : Anthony McKinney et al.

Page 1 of 1

It is certified that error appears in the above-identified patent and that said Letters Patent is hereby corrected as shown below:

Claim 4, Column 30, Line 59, "len-2-yl)-3-azabicyclo[3.1.0]hexane is in pharmaceutically" should read: -- len-2-yl)-3-azabicyclo[3.1.0]hexane is in pharmaceutically --

Claim 6, Column 30, Line 66, "acceptable salt form is (1R,5S)-1-(naphthalen-2-yl)-3-" should read: -- acceptable salt form is (1R,5S)-1-(naphthalen-2-yl)-3- --

Claim 8, Column 31, Line 6, "len-2-yl)-3-azabicyclo[3.1.0]hexane, in free or pharmaceu-" should read: -- len-2-yl)-3-azabicyclo[3.1.0]hexane, in free or pharmaceu- --

Claim 9, Column 31, Line 10, "len-2-yl)-3-azabicyclo[3.1.0]hexane, in free or pharmaceu-" should read: -- len-2-yl)-3-azabicyclo[3.1.0]hexane, in free or pharmaceu- --

Signed and Sealed this
Thirteenth Day of March, 2018

Andrei Iancu
*Director of the United States Patent and Trademark Office*